United States Patent [19]

Eisenbach et al.

[11] Patent Number: 5,750,102
[45] Date of Patent: May 12, 1998

[54] DOUBLE TRANSFECTANTS OF THE MHC GENES AS CELLULAR VACCINES FOR IMMUNO PREVENTION OF TUMOR METASTASIS

[75] Inventors: Lea Eisenbach; Michael Feldman, both of Rehovot, Israel

[73] Assignee: Yeda Research and Development Co., Ltd., Rehovot, Israel

[21] Appl. No.: 412,512

[22] Filed: Mar. 29, 1995

Related U.S. Application Data

[63] Continuation of Ser. No. 28,293, Mar. 9, 1993, abandoned.

[30] Foreign Application Priority Data

Mar. 13, 1992 [EP] European Pat. Off. ............. 92104382

[51] Int. Cl.$^6$ .................... A61K 35/12; C12N 5/08; C12N 15/06; C12N 15/09
[52] U.S. Cl. ................ 424/93.21; 424/93.7; 435/69.6; 435/325; 435/347; 435/366; 935/71
[58] Field of Search ................ 424/93.1, 93.2, 424/93.21, 93.7; 435/240.21, 172.3, 69.5, 69.52, 69.6, 240.1, 240.2; 935/34, 66, 70, 71

[56] References Cited

PUBLICATIONS

Freshney, in "Culture of Animal Cells: A Manual of Basic Technique," Alan R. Liss, Inc., N.Y. 1987 pp. 9 and 10.
Roemer et al. 1992 Eur J. Biochem 208:211–225.
Ledley 1991 Human Gene Therapy 2:77–83.
Ostrand–Rosenberg et al. 1991 Int J Cancer Supplement 6:61–68.
Cordon–Cardo et al. 1991 Cancer Research 51:6372–6380.
Anderson, 1984 Science 226:401–409.
Rodriguez et al. (ed) 1988 in "Vectors: A Survey of Molecular Cloning Vectors and Their Uses", Butterworths, Boston pp. 467–513.
F. Brodsky et al., *Annu. Rev. Immunol.* 9:707–744 (1991).
L. Eisenbach et al., *Haematology & Blood Tran.* 29:499–507, Modern Trends in Human Leukemia VI (1985).
L. Eisenbach et al., *Int. J. Cancer* 32:113–120 (1983).
L. Eisenbach et al., *Immunomodulation of Tumor Metastases (in New Exp. Modalities in the Cont. of Neoplasia)* pp. 81–90 (1986).
L. Eisenbach et al., *Seminars in Cancer Biology* 2:179–188 (1991).
I. Fidler et al., *Science* 197:893–895 (1977).
C. Gelber et al., *Cancer Research* 49:2366–2373 (1989).
L. Hood et al., *Ann. Rev. Immunol.* 1:529–568 (1983).
D. Perkins et al., *J. Exp. Med.*, 170:279–289 (1989).
D. Plaskin et al., *Proc. Natl. Acad. Sci. USA* 85:4463–4467 (1988).

*Primary Examiner*—Brian R. Stanton
*Attorney, Agent, or Firm*—Kohn & Associates

[57] ABSTRACT

The present invention relates to anti-tumor vaccines comprising at least one type of tumor cell into each of which at least two genes encoding MHC proteins of different haplotypes have been inserted, or naturally expressed, said genes being expressed in said tumor cells and wherein at least one of said MHC proteins has the same haplotype as a haplotype of the individual to be vaccinated. The invention furthermore relates to a method of treating a patient suffering from a tumorous disease comprising administering a vaccine of the invention and to the use of a vaccine of the invention for the preparation of an anti-tumor vaccine.

14 Claims, 11 Drawing Sheets

DOUBLE TRANSFECTANTS OF THE MHC GENES AS CELLULAR VACCINES FOR IMMUNO PREVENTION OF TUMOR METASTASIS

This is a continuation of application(s) Ser. No. 08/028,293 filed on Mar. 9, 1993, now abandoned.

TECHNICAL FIELD

1. Field of the Invention

The present invention relates to anti-tumor vaccines comprising at least one type of tumor cell into each of which at least two genes encoding MHC proteins of different haplotypes have been inserted, said genes being expressed in said tumor cells and wherein at least one of said MHC proteins has the same haplotype as a haplotype of the individual to be vaccinated. The invention furthermore relates to a method of treating a patient suffering from a tumorous disease comprising administering a vaccine of the invention and to the use of a vaccine of the invention for the preparation of an anti-tumor vaccine.

2. Description of the Prior Art

Metastasis is a process whereby multiple and widespread tumor colonies are established by malignant cells which have detached from the original tumor (primary tumor) and spread throughout the body. The generation of metastases is a multistep process. For this process to occur, malignant cells must first detach from the primary tumor and invade the extracellular matrix, second, penetrate through the endothelial basement membranes to enter the body cavities and vessels thus spreading all over the body, third, infiltrate target organs including, in many cases, specific recognition of target organs, and, fourth, manipulate the new environment to induce angiogenesis.

Within a single tumor, metastatic as well as non-metastatic cells may exist (e.g. Filder and Kripke, Science 197 (1977), 893–895). It now seems that non-metastatic cells of a metastatic tumor may lack one, a few or all of the properties endowing metastatic cells involved in metastatic growth. Therefore, the transformation process itself may be due to several independent molecular or biochemical changes within the cell which also may be, but are not necessarily, involved in the generation of the metastatic phenotype.

On the other side, development of malignant tumor represents not only neoplastic transformation but also the failure of the host defense system to efficiently eliminate tumor cells. Transformed cells express different tumor-associated antigens (TAAs) that may induce the host immune system to respond appropriately.

From all circulating tumor cells generated only about 0.1% survive. These, however, are sufficient to form metastatic colonies thus giving rise to the mortality of the host. It has been demonstrated that the immune response of a mammalian host against tumor cells may be launched via the proliferation and action of specific cytotoxic T cells (CTLs) which recognize the complex of TAA derived peptides and MHC class I molecules. It is thus intriguing to speculate that for some reason these T cells are no longer able to recognize or interact with the tumor cells.

For example, it has been shown that reduced expression of class I antigens on the transformed cells causes a decrease of immunogenicity of these cells with respect to a CTL mediated immune response (L. Eisenbach and M. Feldman, Seminars in Cancer Biology 2 (1991), 179–188).

Consequently, the mechanism by which tumor cells escape detection and elimination by the immune system may be based on the fact that by virtue of a suboptimal presentation of TAAS, which in turn is caused by a reduced presence of MHC class I molecules on the cell surface, a corresponding proliferative response of CTLs is not set on.

Furthermore, in homozygous syngeneic murine systems it has been found that metastatic tumor cells express less MHC class I molecules on their surface than non-metastatic cells (Eisenbach et al., Int. J. Cancer 32 (1983), 113–120). To test whether the low expression of class I molecules is causally related to the metastatic phenotype of the tumor cells, experiments were carried out to induce modulations in the class I expression and test whether such modulations would result in changes in the metastatic potency of the tumor cells. For these experiments metastatic cells of the Lewis lung carcinoma were used which express low levels of H-2K$^b$ molecules. In vitro treatment of said cells with γ-interferon transiently activated the expression of the H-2K$^b$ gene in the metastatic cells. When these cells were injected into mice, a significant decrease in their metastatic competence was observed (Eisenbach and Feldman, "Genes and antigens controlling tumor metastasis" in: Hematology and Blood Transfusion: Modern Trends in Human Leukemia IV, eds. R. Neth et al., 1985, 499–507; Eisenbach et al. "Immunomodulation of tumor metastases" in "New experimental modalities in the control of neoplasia", ed. Chanandra, 1985, 81–90).

Moreover, transfection of 3LL Lewis lung carcinoma and B16 melanoma cells of metastatic phenotype with H-2K genes resulted in the conversion of these cells to a non-metastatic phenotype which elicited high levels of TAA specific CTLs. It was also shown that the abolishment of the metastatic competence following H-2K gene insertion was a function of the acquisition by the transfectants of H-2K restricted immunogenic potency because the H-2K transfectants generated metastases when injected into athymic nude mice.

Injection of the H-2K transfectants following their inactivation by X-rays and/or mitomycin C into normal syngeneic mice protected the latter from the generation of metastasis by a subsequent graft of cells of the highly metastatic phenotype. Finally, it has been shown that a series of injections of inactivated H-2K transfectants to tumor-bearing animals either decreased or abolished the generation of metastasis.

When the above experiments carried out in homozygous syngeneic mouse systems were repeated in semi-allogeneic heterozygous systems, it was demonstrated that H-2K$^b$ transfectants tested in (H-$2^b$×H-$2^k$)F$_1$ mice and in (H-$2^b$×H-$2K^{bm1}$)F$_1$ mice did neither manifest abolishment or suppression of their metastatic competence nor became immunogenic in F$_1$ hybrids to induce protection against metastasis formation.

Another set of experiments aimed at generating a vaccine against metastasis formation was carried out with single transfectants which were injected into syngeneic homozygous mice. With this system, prevention of metastasis formation was obtained.

The results from the different sets of experiments described above may be summarized in that vaccination was only effective, although not in all cases, if the recipient was of syngeneic homozygous background. Anti-tumor vaccination of humans, however, requires the design of a vaccine which is effective on a heterozygous background.

SUMMARY OF THE INVENTION

Thus, the technical problem underlying the present invention was to provide an anti-tumor vaccine which is effective in the prevention of metastasis formation by cells derived from a primary tumor, and/or the size reduction of the primary tumor in a patient; and to provide a method for treating a patient suffering from a tumorous disease.

The solution to the above technical problem is achieved by providing the embodiments characterized in the claims.

Accordingly, the present invention relates to an anti-tumor vaccine which comprises (a) at least one type of tumor cell into each of which at least two genes encoding MHC proteins of different haplotypes have been inserted, wherein said genes are expressed in said tumor cells and at least one of said MHC proteins has the same haplotype as a haplotype of the individual to be vaccinated; and (b) optionally a pharmaceutically acceptable carrier and/or diluent.

The term "anti-tumor vaccine" refers to a vaccine which is appropriate to prevent the formation of metastasis by cells derived from a primary tumor. The cells derived from a primary tumor may be obtained from a tumor which has been surgically removed. They may also be derived from the ascites of tumor-bearing patients or from existing cell lines of patients with the same type of cancer. Other methods of obtaining said cells are conceivable and may be carried out by the person skilled in the art according to standard procedures.

It also refers to a vaccine which prevents tumor and/or metastasis formation upon subsequent contact with or subsequent generation of a malignant cell in the vaccinated individual. The term "anti-tumor vaccine" as used herein may also comprise a composition which upon administration to a patient from whom a primary tumor was surgically removed, leads to the reduction in size or erasure of a recurrent primary tumor. The term "haplotype of the individual to be inserted" refers to the sequence of histocompatibility genes along one chromosome.

In view of the results previously obtained and discussed above, it has now surprisingly been found that transfection of tumor cells with two different MHC genes, at least one of which matches a haplotype of the individual to be vaccinated and subsequent vaccination leads to a protective immune response. Thus, transfection of the two parental MHC haplotypes into cells of highly metastatic phenotype and subsequent graft of these transfectants into tumor-bearing recipients with a matched haplotype leads to the complete abolishment of spontaneous metastasis formation. Furthermore, in about 60% of the the recipients, even the local tumor was immunologically rejected. Recipients that had rejected the local graft of the double transfectants retained a state of effective immune memory for at least five months following graft rejection: A subsequent graft after 5 months of highly metastatic cells after a booster immunization with double transfectants resulted in the rejection of the metastatic cells.

These tests were carried out in a murine system using the highly metastatic clone D122 of the Lewis lung (3LL) carcinoma. Cells of this clone were transfected with (1) H-2$K^b$+H-2$K^k$ genes and subsequently grafted to (H-2$^b$×H-2$^k$)F$_1$ mice; (2) H-$_2$K$^b$+H-2$K^d$ genes and then grafted to (H-2$^b$×H$_2$$^d$)F$_1$ mice; and (3) H-2$K^b$+H-2$K^{bm1}$ genes and subsequently tested in (H-2$^b$×H-2$^{bm1}$)F$_1$ mice.

Further experiments employing the homozygous mouse strain C57BL/6 (H-2$^b$) from which the highly metastatic clone D122 originates for transplantation studies using H-2$K^b$+H-2$K^k$, H-2$K^b$+H-2$K^d$ or H-$_2$K$^b$+H-2$K^{bm1}$ double transfected D122 cells leads to 60 to 70% rejection of most grafts. Of the grafted cells that grew out to a local tumor, none developed any metastasis. This result could be repeated with double transfectants which were injected intravenously.

Animals that had been immunized with inactivated double transfectants did not develop metastasis when subsequently grafted with cells from the parental clone D122. In contrast, the corresponding vaccination with single transfectants did not prevent subsequent metastasis formation.

Surprisingly, the rejection of the double transfectants by homozygous C57BL/6 mice cannot be attributed to an immune response to the alloantigen per se, because H-2$K^k$ or H-2$K^d$ single transfectants were not rejected. It rather appears that co-expression of alloantigens with syngeneic MHC genes amplifies the immune response against the syngeneic H-2$K^b$-TAA complex as compared to the response elicited by the H-2$K^b$-TAA complex alone. This response is a function of T cell reactivity, since the injection of transfectants into nude mice led to the generation of large masses of lung metastases. The amplification of said response may be due to the action of cytokines (e.g. IL-2) secreted in response to the strong reaction against the alloantigen. The cytokines may act in augmenting the response against the syngeneic H-2K-TAA complex.

In a particularly preferred embodiment the tumor cell comprised in the anti-tumor vaccine of the present invention is a human tumor cell. Said vaccine is administered to human patients. Since the MHC systems, the presentation of antigens and the corresponding immune responses in humans and in mice are highly homologous (for a recent review see F. M. Brodsky and L. E. Guagliardi, "The Cell Biology of Antigen Processing and Presentation", Annu. Rev. Immunol. 9 (1991), 707–744), the results herein obtained with murine models show the applicability of the invention to human vaccines.

Accordingly, any human bearing a malignant tumor may be vaccinated with tumor cells transfected with MHC genes wherein at least one of the MHC proteins expressed by said genes has the same haplotype as a haplotype of the patient. The MHC genes may be cloned from cells or tissue from said patient or from any normal tissue of the same haplotype and inserted into suitable expression vectors according to standard procedures (Hood et al., Annu. Rev. Immunol. 1 (1983), 529–568, and references cited therein; Sambrook et al., Molecular Cloning, 2nd edition 1989, Cold Spring Harbor Laboratory, Cold Spring Harbor). Transfection conditions, preparation of transfectants for administration to patients and suitable conditions for administration are also selected or carried out according to routine standards or may be determined by the physician involved in the respective case.

Said vaccination may be used in order to treat cancer patients to prevent and/or inhibit the formation of metastases. Said prevention will be effected if the primary tumor has not elicited any metastasis formation. However, even if metastasis formation has been progressed before administration of the vaccine of the invention, further metastasis formation may be inhibited by treatment with the vaccine of the invention. In particular, the following protocol for the treatment of cancer patients may be envisaged: Following diagnosis of the primary tumor, said tumor is surgically removed. After surgical removal of the local tumor, vaccination is initiated using double transfected tumor cells. The vaccination at this stage aims at (a) preventing metastasis formation by cells which migrated out of the tumor prior to surgery, and (b) preventing recurrence of new primary tumors, particularly in cases of breast cancer, melanomas, etc., where such recurrences take place.

Furthermore, treatment with the vaccine of the invention may lead to the reduction in size or the eradication of recurrent primary tumors or of already existing metastases in humans. Repeated vaccination will result in the generation of an immunological memory; thus, the formation of metastases which derive from the tumor at a later stage of the disease will equally be avoided by treatment with the vaccine of the invention.

In another preferred embodiment the tumor cell comprised in the vaccine of the invention is derived from a tumor cell having metastatic competence. The term "metastatic competence" refers to the feature of said tumor cell to be able to detach from the primary tumor and eventually form at a different location in the body a secondary tumor (metastasis). Although said tumor cell has said metastatic competence, it does not necessarily detach from the primary tumor to form a metastasis.

In a further preferred embodiment the tumor cell comprised in the vaccine of the invention is derived from a tumor cell having substantially no metastatic competence. The term "having substantially no metastatic competence" defines the state of said tumor cell which in its present physiological and genetic state will not generate metastasis. Thus, as described hereinbefore, said tumor cell will have all the features of a neoplastic cell, but will not display the additional features of a cell with metastatic competence. It cannot, however, be excluded that such a tumor cell will, under appropriate circumstances, be induced to become a tumor cell of metastatic phenotype. Besides the prophylaxis of metastasis formation the vaccine of the present invention may be used in the treatment of recurrent primary tumors. In particular, treatment with the vaccine of the present invention may lead to a reduced size or, under especially favorable conditions, to the erasure of recurrent primary tumors.

A particularly preferred embodiment of the present invention relates to an anti-tumor vaccine wherein said genes encode human MHC class I (HLA-A, HLA-B or HLA-C) proteins. In most cancers, the immune response thereto is dominated by the activity of cytotoxic T lymphocytes (CTLs). CTLs predominantly recognize antigens such as TAAs when presented by MHC class I molecules. Transfection of tumor cells with MHC class I molecules will therefore result in an improved capacity of tumor cells which normally have a reduced amount of MHC class I molecules on their surface to present TAAs to the immune system, notably to CTLs. Whereas due to the low density of antigen presenting MHC class I molecules on the surface of tumor cells, said cells may escape the mechanism of effective immune surveillance, an increased number of antigen presenting molecules as a result of the transfection will temporarily efficiently expose the antigens to the immune system. This exposure is sufficient to launch an immune response represented by the proliferative response of TAA specific CTLs. It is, moreover, sufficient to establish at least the first step of an immunological memory. Thus, a booster injection with MHC class I transfected tumor cells and subsequent contact of the immune system with non-transfected tumor cells will be efficient in the prevention of metastasis formation.

In still another particularly preferred embodiment the genes encoding MHC proteins comprised in the anti-tumor vaccine of the invention encode human MHC class II (HLA-DR, HLA-DQ or HLA-DP) proteins. It has been known in the art for some time that tumor-bearing hosts display both a cell-mediated and a humoral immune response to their tumor-antigens (see, e.g., Hood et al. "Immunology", 2nd edition, 1984, The Benjamin/Cummings Publishing Company, Inc., Menlo Park Calif.). In particular, the immune response against leukemias may be triggered by antigen presentation via MHC class II proteins. Moreover, recent experiments have demonstrated that some antigens may be presented by both MHC class I and MHC class II proteins (Perkins et al., J. Exp. Med. 170 (1989), 279–289) and that class II molecules are more versatile with respect to the source of antigenic peptides presented than class I molecules (Brodsky and Guagliardi, ibid.). Thus, it is to be expected that a number of different TAAS, especially those specific for leukemias are presented by MHC class II molecules. A reduced amount of MHC class II molecules on the surface of antigen presenting cells may, as has been shown in the case with MHC class I molecules, result in an inappropriate or non-existing immune response. Again, as is the case with MHC class I molecules, an increase in the number of antigen presenting molecules may induce a $T_H$-dependent (class II restricted) protective immune response.

A further preferred embodiment of the present invention relates to an anti-tumor vaccine wherein said genes encoding said MHC proteins and being inserted into said tumor cell have been introduced on a single expression vector enabling constitutive production of said MHC proteins in vivo. The term "enabling constitutive production of MHC proteins in vivo" refers to the capability of said vectors to drive the expression of MHC proteins from a suitable promoter after transfection of the recombinant vector and after the transfectants have been grafted to or injected into a patient in need of an anti-cancer treatment. An expression vector suitable for the generation of the vaccine of the invention may be designed by the person skilled in the art according to standard procedures (see, e.g., Sambrook et al., ibid.). Of particular importance in the design of such a vector is the choice of a suitable promoter enabling constitutive expression of the respective MHC proteins in vivo. Examples of said promoters are native promoters of MHC genes, the β-actin promoter and viral promoters.

In another preferred embodiment of the vaccine of the present invention said genes encoding said MHC proteins and inserted into said tumor cell have been introduced on different expression vectors enabling constitutive production of the MHC proteins in vivo. The person skilled in the art is familiar with the design of both single and co-transfection experiments. A detailed description of such experiments is to be found e.g. in Sambrook et al., ibid. The choice of whether the different MHC molecules will be introduced into the tumor cells on a single or on different plasmids will, for example, depend on the cloning strategy and/or the pre-existence of available recombinant expression vectors carrying genes encoding MHC proteins.

In a particularly preferred embodiment of the vaccine of the present invention said expression vector is a plasmid.

In another particularly preferred embodiment of the vaccine of the present invention said expression vector is a retroviral vector. The choice of whether to employ a plasmid or a retroviral vector is made by the person skilled in the art according to considerations which take into account the nature of the target cells and the kinetics of their proliferation in vitro.

In a further embodiment of the vaccine of the invention said genes have been integrated into the chromosomes of said tumor cell.

In still another embodiment of the vaccine of the present invention, said genes are episomally retained in said tumor cell.

Whether said genes encoding the MHC proteins will be integrated into the chromosome of said tumor cell or will be retained episomally will be mainly dependent on the vector employed in the cloning and subsequent transformation and expression of said genes.

A further embodiment of the present invention relates to a vaccine wherein said tumor cell has been inactivated. The term "inactivation" refers to exposure to irradiation, to mitomycin treatment, or treatment with cross-linkers of proteins, such as glutaraldehyde, which preserve the immunogenic properties of cell surface antigens.

Inactivated tumor cells may advantageously be employed in the vaccine of the present invention because of safety requirements. The tumor cells used for transfection will be inactivated prior to vaccination and will not be capable of proliferation in vivo.

In a particularly preferred embodiment of the vaccine of the present invention said tumor cells have been inactivated by treatment with X-rays and/or mitomycin C. Treatment with X-rays or treatment with mitomycin C may be used alone or in combination for the inactivation of transfected tumor cells. Inactivation is effected after transfection. A detailed inactivation protocol for MHC class I transfected tumor cells is given in Example 5 hereinbelow.

In a further preferred embodiment of the present invention, said MHC protein encoding genes have been inserted into said tumor cell by transfection. Transfection of MHC genes is particularly advantageous for the generation of modified tumor cells to be used in the vaccine of the present invention since transfection protocols have been well established in many laboratories and may conveniently be manipulated for a particular use (for a review see, e.g., Sambrook et al., ibid.).

In a further preferred embodiment, the vaccine of the present invention comprises $1 \times 10^6$ to $1 \times 10^9$ tumor cells. The actual number of transfectants formulated in the vaccine of the invention will depend on the disease status of the patient in need thereof.

It may further more depend on the number of antigen presenting molecules normally expressed on the surface of said tumor cells, the type and class of MHC molecule involved in the presentation of antigen and on the efficiency of the presentation of the TAAs by said MHC molecules to the immune system.

The physician involved in the respective case will be able to adjust the dosage of transfected tumor cells contained in the vaccine of the invention for optimal results, if the first administrations did not show the desired results.

In a particularly preferred embodiment the vaccine of the present invention comprises $1 \times 10^7$ tumor cells.

In another preferred embodiment of the present invention said vaccine is formulated as an injectable solution. The term "injectable solution" refers to a formulation of the vaccine which will render it appropriate for parenteral administration, e.g., intravenous, intraperitoneal, subcutaneous, intramuscular, intrathecal, intraorbital, intracapsular, intraspinal or intrasternal injection. The route of injection will generally depend on the type of tumor to be treated. The injectable solution may comprise additionally to an effective a mount of transfected tumor cells any pharmaceutically and/or physiologically acceptable solution, such as phosphate buffered saline which may be chosen by the physician handling the case according to standards known in the art.

As a rule, the physician entrusted with the case will decide on the appropriate way for the administration and the formulation of the vaccine.

Another object of the invention is to provide a method of treating a patient suffering from a tumorous disease comprising administering a vaccine of the invention.

Still another object of the invention is to use a tumor cell transfected with at least two genes encoding MHC proteins of different haplotypes wherein said genes are expressed in said tumor cells and at least one of said MHC proteins has the same haplotype as a haplotype of the individual to be vaccinated and optionally supplemented or treated as described hereinbefore for the preparation of an anti-tumor vaccine.

The numbers in the figure indicate the fraction of mice that grew tumors.

Figure 6:
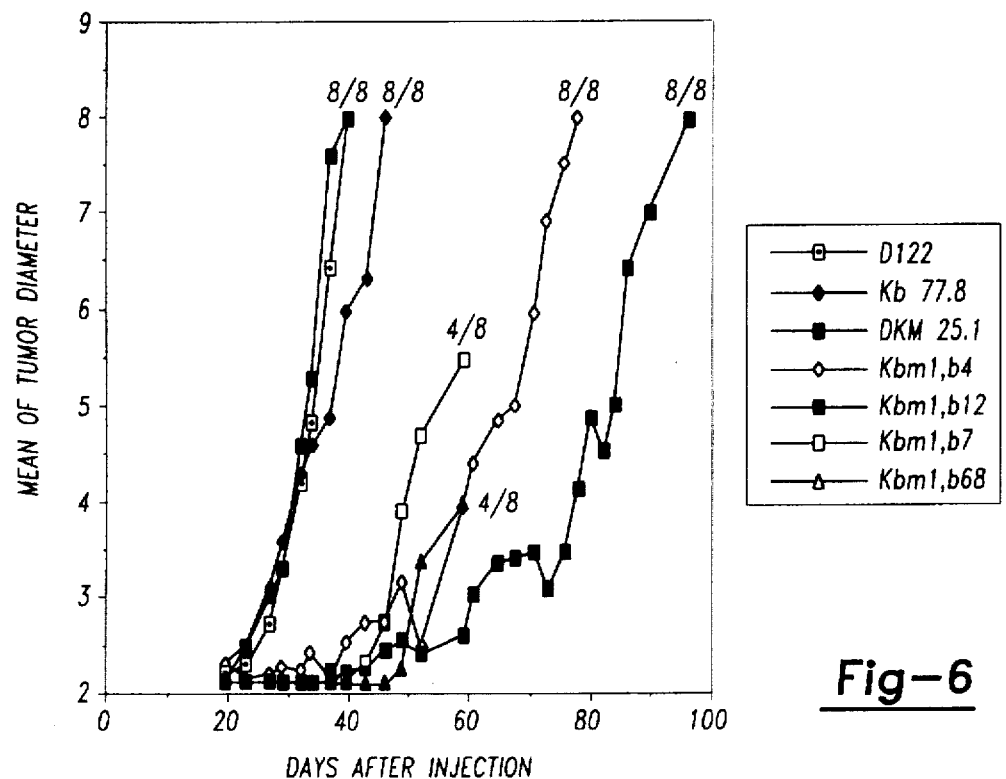

FIG. 6: Growth curves of D122, $K^b77.8$, DKM25.1, and $K^b,K^{bm1}$ transfectants in C57BL/6 mice. C57BL/6 mice were injected i.f.p. with $2 \times 10^5$ cells/mouse and growth rate was measured as described in Example 10. Tumor size is expressed by diameter of the tumor-bearing foot pad. The clone $K^{bm1}25.1$ is also named DKM 25.1. The numbers in the figure indicate the fraction of mice that grew tumors.

Figure 7:
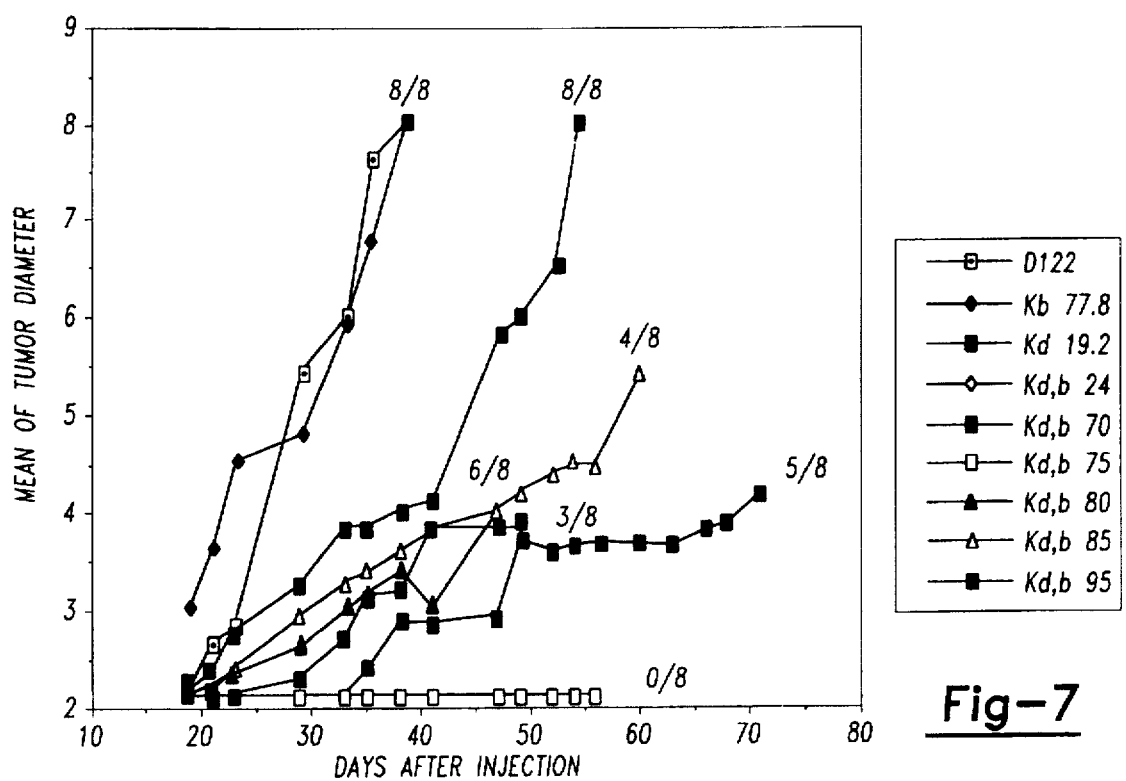

FIG. 7: Growth curves of D122, single transfectants and $K^b,K^d/D122$ double transfectants in CB6/F1 mice. CB6/F1 mice were injected i.f.p. with $2 \times 10^5$ cells/mouse and growth rate was measured as described in Example 11. Tumor size is expressed by diameter of the tumor-bearing foot pad. The numbers in the figure indicate the fraction of mice that grew the primary tumor.

Figure 8:
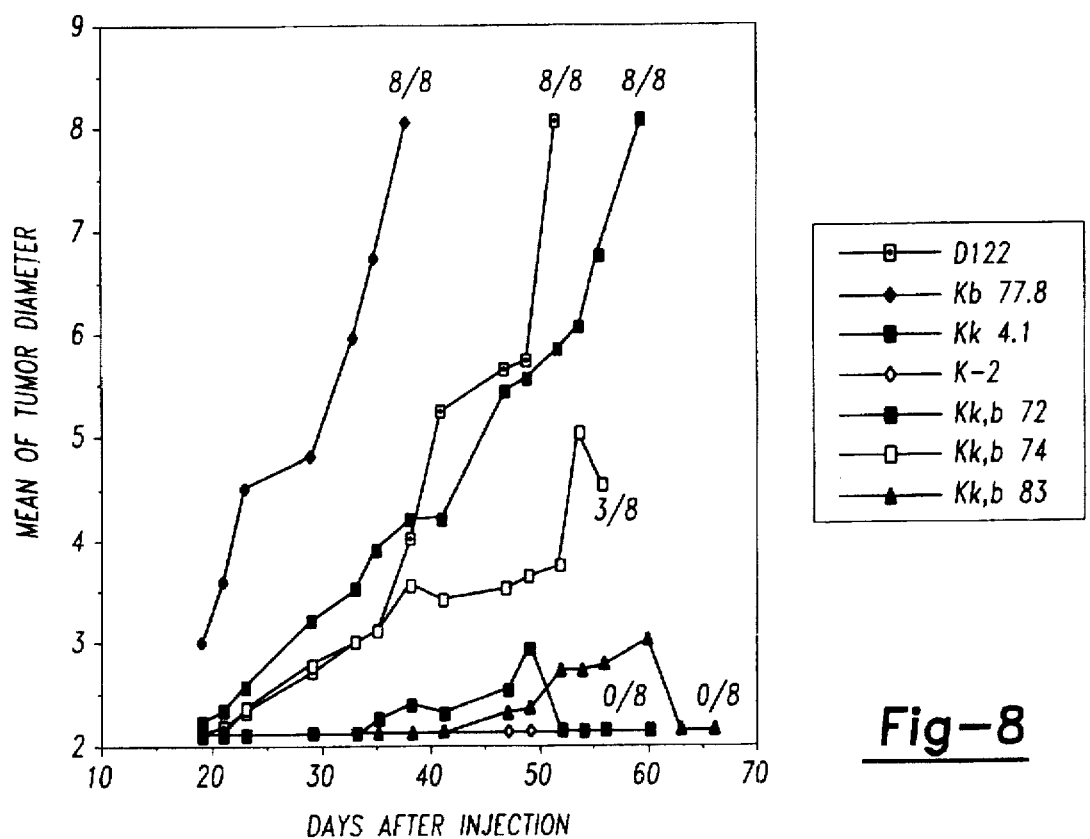

FIG. 8: Growth curves of D122, single transfectants and $K^b, K^k/D122$ double transfectants in C3B6/F1 mice. C3B6/F1 mice were injected i.f.p. with $2 \times 10^5$ cells/mouse and growth rate was measured as described in Example 11. The numbers in the figure indicate the fraction of mice that grew the primary tumor. The transfectants Kk.b72, Kk.b83, and K-2 did not grow at all (0/8).

Figure 9:
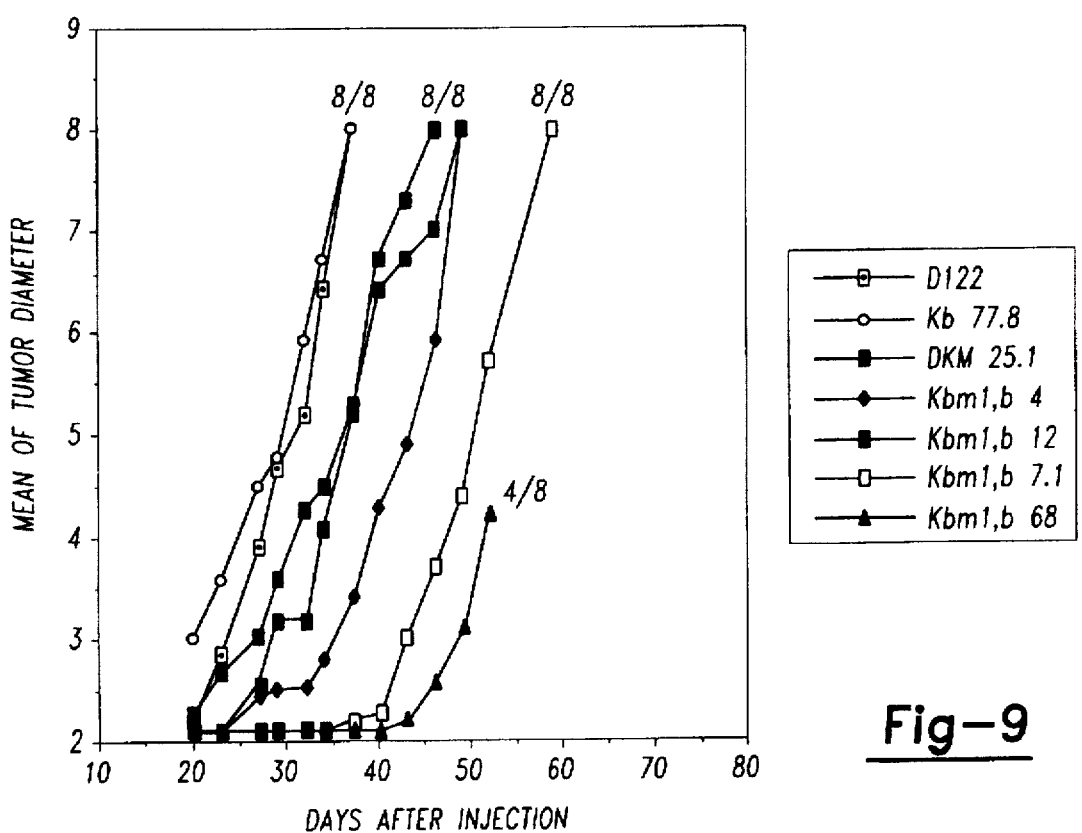

FIG. 9: Growth curves of D122, single transfectants and $K^b K^{bm1}/D122$ double transfectants in (BL×BM1)F1 mice. (BL×BM1)F1 mice were injected i.f.p. with $2 \times 10^5$ cells/mouse and growth rate was measured as described in Example 11. Tumor size is expressed by diameter of the tumor-bearing foot pad. The numbers in the figure indicate the fraction of mice that grew the primary tumor. The clone $K^{bm1}25.1$ is also named DKM 25.1.

Figure 10:
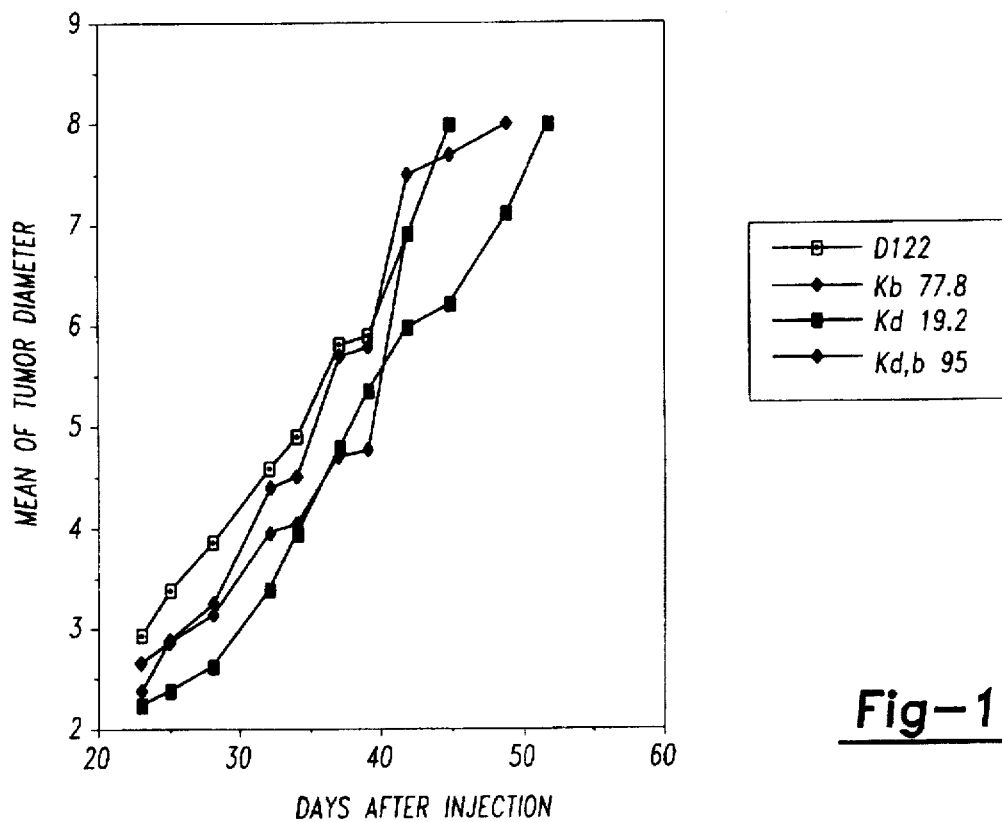

FIG. 10: Growth curves of D122, single transfectants and $K^b, K^d/D122$ double transfectants in nude mice.

Nude mice were injected i.f.p. with $2 \times 10^5$ cells/mouse and growth rate was measured as described in Example 12. Tumor size is expressed by the diameter of the tumor-bearing foot pad.

Figure 11:
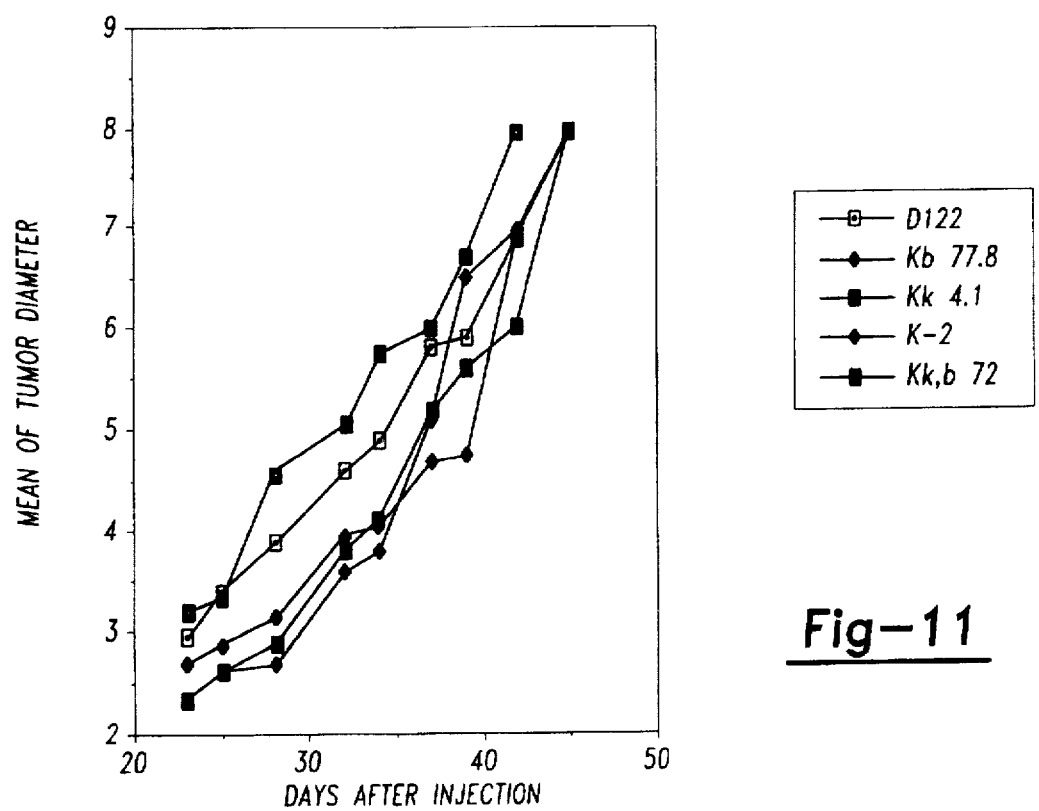

FIG. 11: Growth curves of D122, single transfectants and $K^b, K^k/D122$ double transfectants in nude mice.

Nude mice were injected i.f.p. with $2 \times 10^5$ cells/mouse and growth rate was measured as described in Example 12. Tumor size is expressed by the diameter of the tumor-bearing foot pad.

Figure 12:
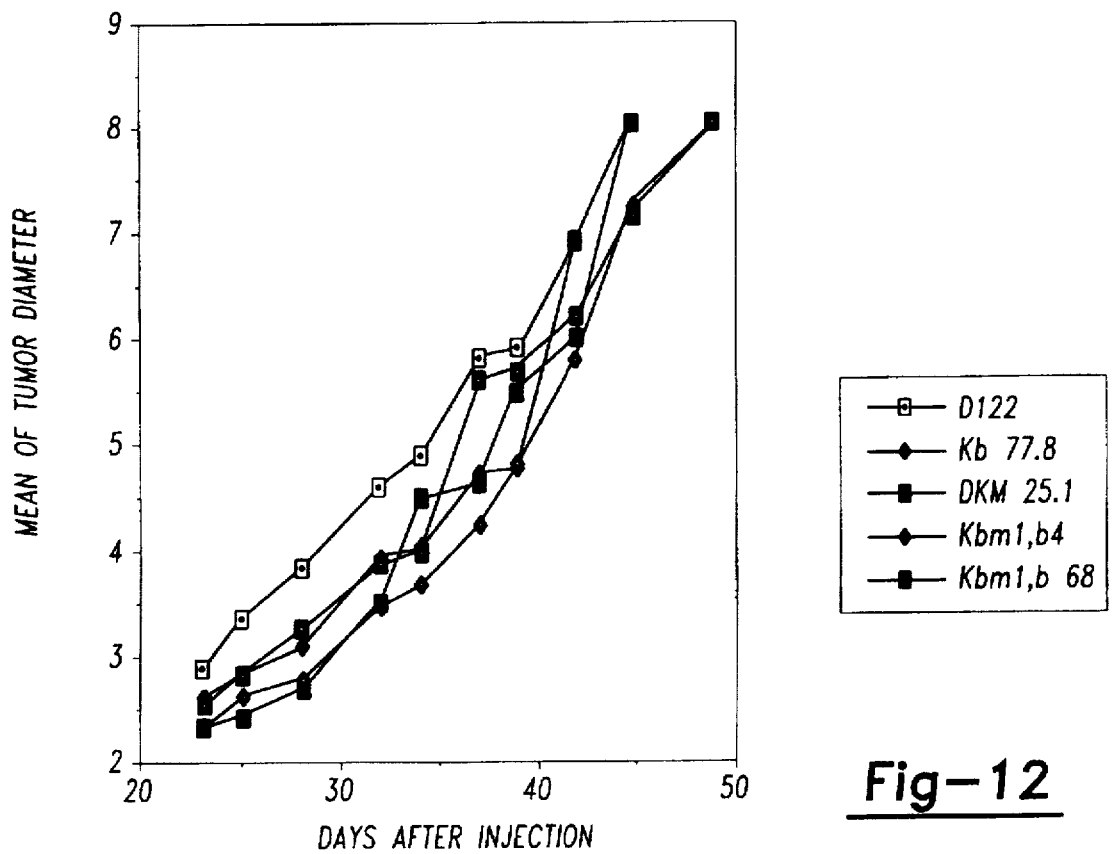

FIG. 12: Growth curves of D122, single transfectants and $K^b, K^{bm1}/D122$ double transfectants in nude mice.

Nude mice were injected i.f.p. with $2 \times 10^5$ cells/mouse and growth rate was measured as described in Example 12. Tumor size is expressed by the diameter of the tumor-bearing foot pad.

The clone $K^{bm1}25.1$ is also named DKM 25.1.

Figure 13:
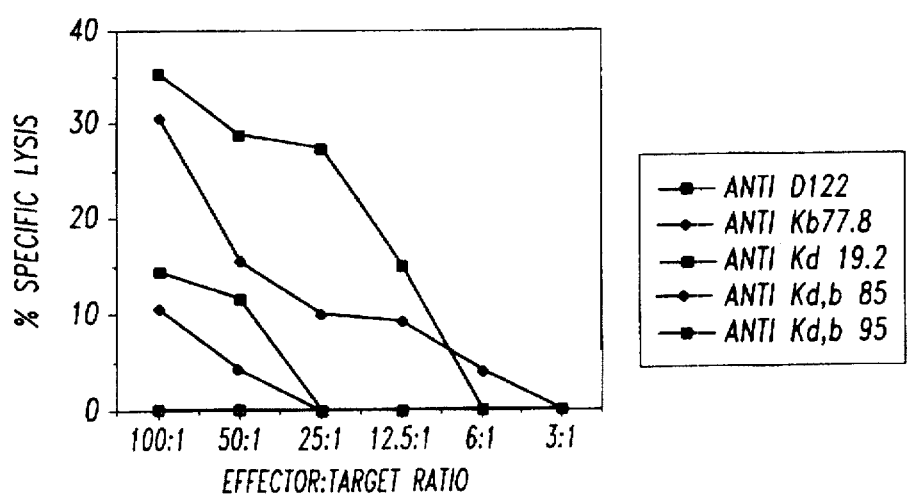

FIG. 13: In vitro lytic activity of CTLs elicted by D122, single transfectants ($K^b77.8$ and $K^d19.2$) and double transfectants (Kd.b85 and Kd.b95). C57BL/6 mice were immunized three times at 7-day intervals by i.p. injection of $2 \times 10^6$ irradiated and mitomycin-c treated cells. 10 days later, spleen cells were restimulated in vitro with the same tumor cells, irradiated and mitomycin-C treated as before for 5 days (see Example 15). Cytolytic activity was determined at different effector-to-target ratios against $^{35}S$ methionine labeled D122 target cells in a 16-hour assay.

Figure 14:
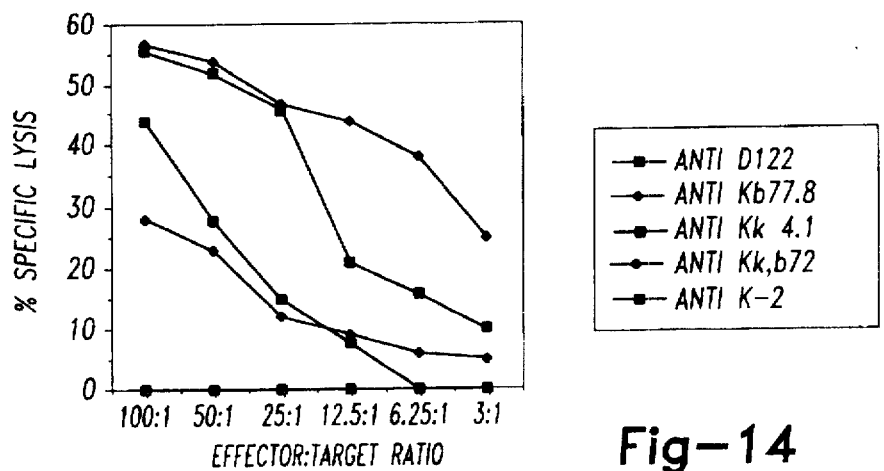

FIG. 14: In vitro lytic activity of CTLs elicited by D122, single transfectants ($K^b77.8$ and $K^k4.1$) and double transfectants (K-2 and Kk.b72). C57BL/6 mice were immunized three times at 7-day intervals by i.p. injection of $2 \times 10^6$ irradiated and mitomycin-C treated cells. 10 days later, spleen cells were reswithlated in vitro with the same tumor cells, irradiated and mitomycin-C treated as before for 5 days (see Example 15). Cytolytic activity was determined at different effector-to-target ratios against $^{35}S$ methionine labeled D122 target cells in a 16-hour assay.

Figure 15:
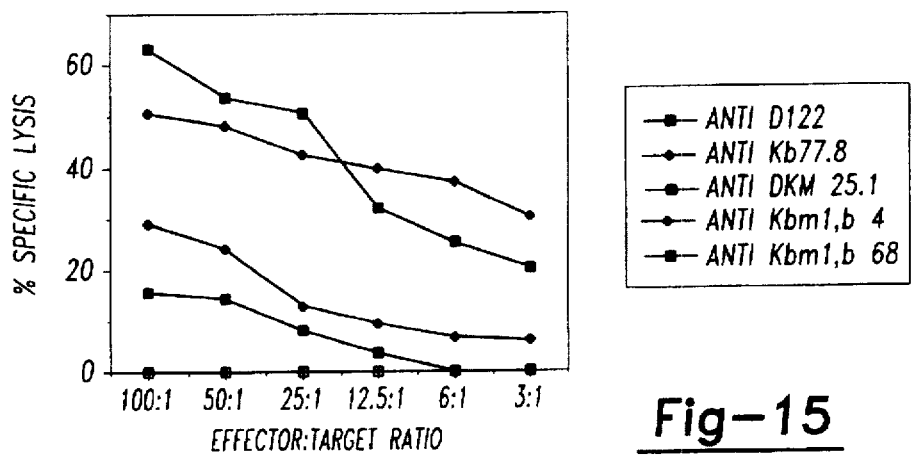

FIG. 15: In vitro lytic activity of CTLs elicited by D122, single transfectants ($K^b77.8$ and DKM 25.1) and double transfectants (Kbm1.b4 and Kbm1.b68). C57BL/6 mice were immunized three times at 7-day intervals by i.p. injection of $2 \times 10^6$ irradiated and mitomycin-C treated cells. 10 days later, spleen cells were restimulated in vitro with the same tumor cells, irradiated and mitomycin-C treated as before for 5 days (see Example 15). Cytolytic activity was determined at different effector-to-target ratios against $^{35}S$ methionine labeled D122 target cells in a 16-hour assay. $K^{bm1}25.1$ is also named DKM 25.1.

Figure 16:
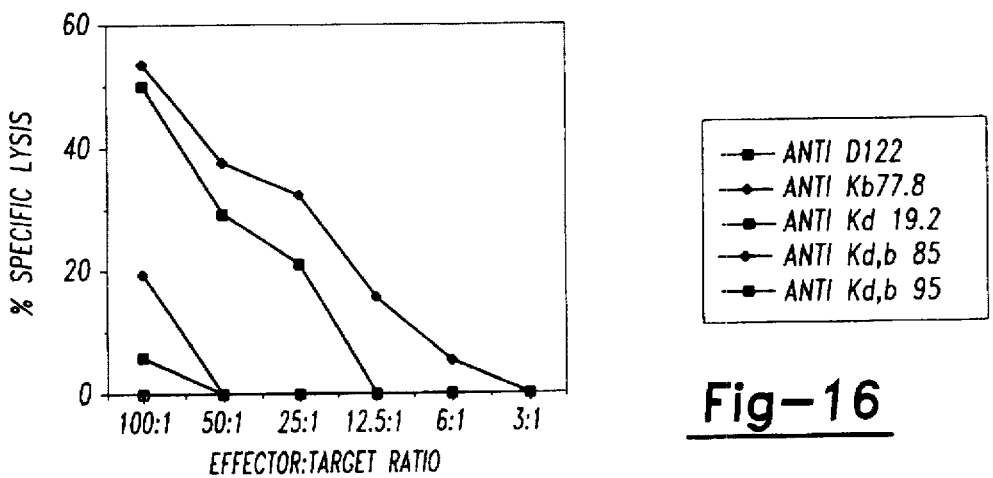

FIG. 16: In vitro lytic activity of CTLs elicited by D122, single transfectants ($K^b77.8$ and $K^d19.2$) and double transfectants (Kd.b85 and Kd.b95). CB6/F1 mice were immunized three times at 7-day intervals by i.p. injection of $2 \times 10^6$ irradiated and mitomycin-C treated cells. 10 days later, spleen cells were restimulated in vitro with the same tumor cells, irradiated and mitomycin-C treated as before for 5 days (see Example 16). Cytolytic activity was determined at different effector-to-target ratios against $^{35}S$ methionine labeled D122 target cells in a 16-hour assay.

Figure 17:
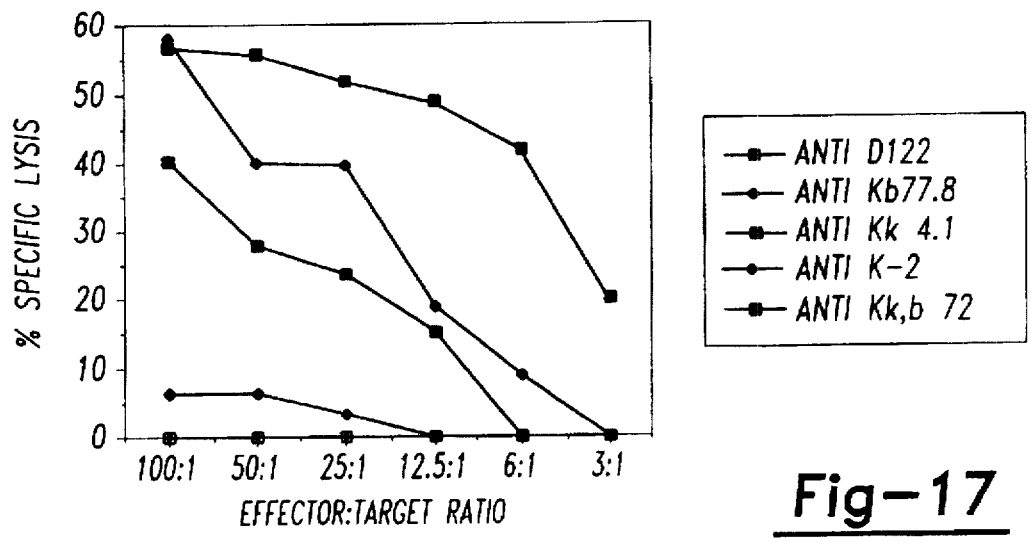

FIG. 17: In vitro lytic activity of CTLs elicted by D122, single transfectants ($K^b77.8$ and $K^k4.1$) and double transfectants (K-2 and Kk.b72). C3B6/F1 mice were immunized three times at 7-day intervals by i.p. injection of $2 \times 10^6$ irradiated and mitomycin-C treated cells. 10 days later, spleen cells were restimulated in vitro with the same tumor cells, irradiated and mitomycin-C treated as before for 5 days (see Example 16). Cytolytic activity was determined at different effector-to-target ratios against $^{35}S$ methionine labeled D122 target cells in a 16-hour assay.

Figure 18:
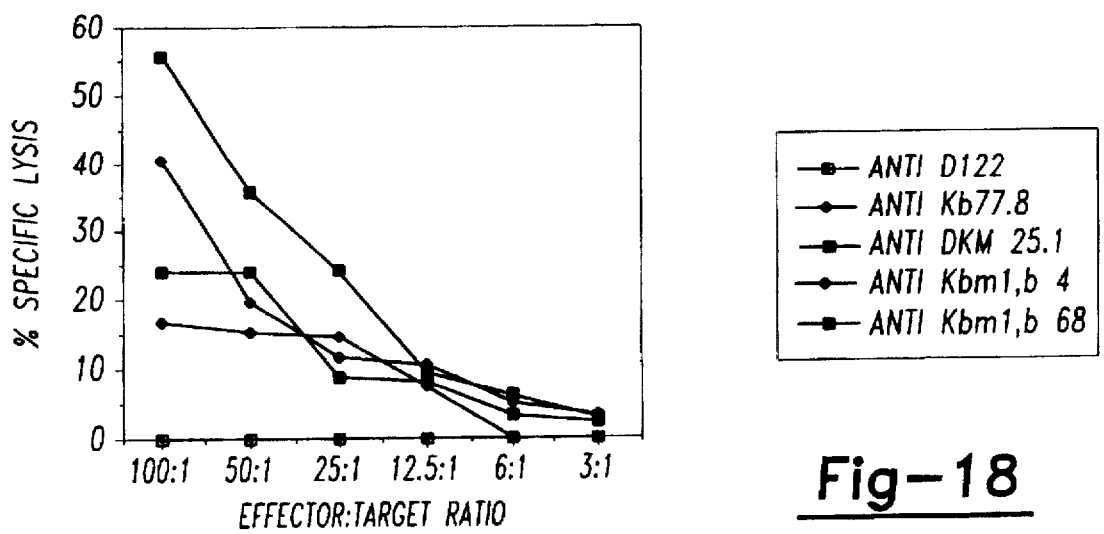

FIG. 18: In vitro lytic activity of CTLs elicted by D122, single transfectants ($K^b77.8$ and DKM 25.1) and double transfectant (Kbm1.b68). (BL×BM1)/F1 mice were immunized three times at 7-day intervals by i.p. injection of $2 \times 10^6$ irradiated and mitomycin-C treated cells. 10 days later, spleen cells were restimulated in vitro with the same tumor cells, irradiated and mitomycin-C treated as before for 5 days (see Example 16). Cytolytic activity was determined at different effector-to-target ratios against $^{35}S$ methionine labeled D122 target cells in a 16-hour assay. $K^{bm1}25.1$ is also named DKM 25.1.

FIG. 19a and b CB6/F1 mice (a) or C3B6/F1 mice (b) were inoculated i.f.p. with $2 \times 10^5$ cells/mouse.

Starting on day 8 after the inoculation, groups of mice were immunized i.p. 4 or 8 times at 7-day intervals with (a) inactivated, parental D122 cells ▨, transfectants Kb39.5 ▥, Kd19.2 ▢ and Kdb85 ▤, and a mixture of the two single transfectants Kb39.5+Kd19.2 (□); or with (b) inactivated D122 cells (▨) transfectants Kb39.5 (▥), Kk4.1 (□), Kkb2 (▧) and Kkb72 (▤) and a mixture of the single transfectants $K^{39.5}$+Kk4.1 (□). Controls for the two groups (a and b) were nonimmunized mice (■). Tumorigenicity and spontaneous metastasis were determined as described in the examples.

Normal lung weight (220 mg) is shown by a dashed line.

DETAILED DESCRIPTION

The examples illustrate the invention.

In the experiments described in the examples, inbred male or female mice, C57BL/6J (H-$2^b$, CB6-(BALB/c×C57BL/6J) F1 (H-$2^d$, H-$2^b$), C3B6-(C3H×C57BL/6J) F1 (H-$2^b$, H-$2^k$), BLXBM1 (B6CH$2^{bm1}$×C57BL) F1 (H-$2^b$, H-$2^{bm1}$) aged 9–12 weeks were used in this study. The mice were purchased directly from Jackson Laboratories U.S.A.

Furthermore, the following tumors were employed: Lewis lung carcinoma: The Lewis lung carcinoma (3LL), which originated spontaneously in a C57BL/6J (H-$2^b$) mouse is a malignant tumor that produces spontaneous lung metastasis in syngeneic recipients. D122 is a highly metastatic clone, cloned from 3LL by limiting dilution (Poste and Filder, Nature 283 (1980), 139–140).

RNA isolation, Northern Blotting, the isolation of genomic and plasmid DNA, restriction digestions, nick translation, hybridization experiments, including those with end labeled oligonucleotides was done according to conventional methods. For a detailed description of said methods see, e.g., Sambrook et al., Molecular Cloning, A Laboratory Manual, Second Edition 1989, Cold Spring Harbor Laboratory, Cold Spring Harbor.

Cultures of 3LL clones were maintained in DMEM, supplemented with 10% heat-inactivated FCS, 2 mM glutamine/1% combined antibiotics, 1 mM sodium pyruvate and 1 mM nonessential amino acids.

Cultures were kept at 37° C in a humidified atmosphere of 5% $CO_2$ in air.

EXAMPLE 1

Assays for analysis of metastatic competence

Assays of experimental lung metastasis

Tumor cells were obtained from tissue culture after trypsinization, and washing with PBS. For 3LL clones (the transfectants and the controls), mice were inoculated with $5 \times 10^5$ tumor cells in 0.5 ml PBS injected via the tail vein (i.v.) 30 days later mice were sacrificed, lungs were excised and metastatic load was evaluated by weight.

Assay of spontaneous lung metastasis

Mice were injected with $2 \times 10^5$ tumor cells intrafootpad (i.f.p.) in the right hind leg. The grafted mice were examined every 1–3 days, and the diameter of the tumor was measured using a caliper. When the tumor reached the diameter of 8 mm, the tumor-bearing leg was amputated. Amputation was performed using a 3/0(2) silk tie, which was ligated below the knee joint of the leg to prevent bleeding. For 3LL clones (the transfectants and the controls) mice were sacrificed 30–35 days after amputation. All lungs were excised and metastatic load was determined as weight of lungs in mg.

EXAMPLE 2

Analysis of H-2 expression of tumor cells

To detect H-2 class I cell surface expression on tumor cells (1) immunofluorescence staining of the cells by specific monoclonal antibodies directed against different H-2 subregions was carried out using the Fluorescence Activated Cell Sorter (FACS 440 Beckon Dickinson, Mountain View, U.S.A.) and (2) direct radioimmunoassays were performed.

Monoclonal antibodies against H-2K$^b$ and H-2K$^d$ were prepared (as ascites fluids) from hybridoma cells. Clones 9-18-10 (anti K$^d$), 20-8-4 (anti K$^b$), K-10-18-9 (anti K$^d$), K-9-178 (anti K$^b$), 28-14-8 (anti D$^b$), and 16-3-1 (anti K$^k$) were used. The fluorescent reagents used in this study were goat antimouse Ig and goat anti-mouse IgM (conjugated to fluorescein isothiocyanate (FITC), purchased from Nordic Immunological Laboratories, Tilburg, Holland).

A sample of $2 \times 10^6$ cells in 0.1 ml PBS was incubated for 60 min at 0° C. with 5 µl of specific monoclonal antibody. After 2 washings with PBS-2% Fetal Calf Serum (FCS), the cells were incubated for 30 min at 0° C. with 20 µl (1:10 diluted) of FITC conjugated goat anti-mouse Ig. After one further washing with PBS-0.1% sodium azide, cells were resuspended in 1 ml PBS 0.1% sodium azide, filtered through nylon mesh no. 120 and analyzed using the fluorescence-activated cell sorter (FACS 440).

The percentage of specific fluorescence positive cells was calculated as follows:

$$\% \text{ Fluorescence positive cells} = \frac{(A-B)}{(100-B)}$$

wherein A is the percentage of the fluorescent cells in the experimental sample tested and B is the percentage of the fluorescent cells in the control sample. The control sample was obtained by incubating the cells with FITC labeled antibodies only.

EXAMPLE 3

Direct R.I.A. analysis of H-2 expression on tumor cells

To detect H-2 class I cell surface expression on tumor cells direct radioimmunoassays were performed using 20-8-4 (anti K$^b$), 16-3-1 (anti K$^k$), 9-18-10 (anti K$^d$), 28-14-8 (anti D$^b$), K-9-178 (anti K$^b$), K-10-18-9 (anti K$^d$), antibodies after iodination with $I^{125}$. Iodination of antibodies was carried out according to standard procedures; see, e.g., Harlow and Lane, Antibodies, A Laboratory Manual, Cold Spring Harbor Laboratory, Cold Spring Harbor 1988. Triplicate samples of $5 \times 10^5$ cells in 0.1 ml PBS were incubated with 0.5 µg labeled antibodies at 0° C. for 120 min. Incubation was done in PBS 0.5% BSA pre-coated tubes. After 4 washings with PBS 0.02% sodium azide, samples were counted in a gamma counter. For the K$^b$+K$^{bm1}$ transfectants direct R.I.As were performed with monoclonal antibodies using K9-178 (an anti K$^b$ antibody not cross-reactive with K$^{bm1}$) and 20-8-4 (binds to both K$^b$ and K$^{bm1}$). K$^{bm1}$ levels were calculated by the difference between binding of antibodies 20-8-4 and K9-178. For the K$^b$+K$^d$ transfectants, direct R.I.As were performed with monoclonal antibodies using K-9-178 (anti K$^b$) and K-10-18-9 (anti K$^d$). For the K$^b$+K$^k$ transfectants, direct R.I.As were performed with monoclonal antibodies using 20-8-4 (anti K$^b$) and 16-3-1 (anti K$^k$). In all types of transfections direct radio-immunoassays were performed with monoclonal antibody 28-14-8 (anti D$^b$).

EXAMPLE 4

Transfection of tumor cells with H-2 class I genes

Co-transfection of clone D122 with: (a) K$^b$+K$^d$; (b) K$^b$+K$^k$; (c) K$^b$+K$^{bm1}$.

Transfections were performed with 20 µg K$^b$ plasmid+20 µg of a second plasmid (K$^k$, K$^d$, K$^{bm1}$, respectively) and 4 µg of plasmid pSV2neo. DNAs were coprecipitated in one Eppendorff tube, dissolved in 1.8 ml sterile water and 200 µl of 2.5M $CaCl_2$ was added. Hepes X2 mix containing 274 mM NaCl, 10 mM KCl, 1.4 mM Na phosphate, 12 mM Dextrose and 40 mM Hepes, pH 7.1, was prepared separately. 2 ml of Hepes X2 were mixed with 2 ml DNA-Ca$^{++}$ solution by slow dripping under $N_2$ gas. DNA precipitates were left for 30 min at room temperature and vortexed before addition to the cells. D122 cells were seeded at $5 \times 10^5$ cell/10 cm dish the night before transfection. The next day media were replaced by 8 ml DMEM-5% FCS. After 5 hours, 2 ml of DNA-Ca phosphate mixture were added to each of duplicated dishes and cells were incubated at 37° C.–5% $CO_2$ for 24 hours.

To increase the efficiency of transfection a DMSO (dimethylsulfoxide) shock was performed. DNA calcium phosphate precipitates were removed and replaced by DMEM-10% FCS containing 15%-DMSO solution for 15 min. After shock treatment DMEM-10% FCS was added for 24–48 hours before Geneticin selection. To select for Geneticin-resistant cells, cells were collected by trypsinization, divided into Costar 24 cluster units ($2 \times 10^4$ cells in each well) and selection medium containing 0.4 mg Geneticin in 1 ml DMEM solution was added. Medium was changed every 3 days. Non-transfectants (D122 cells) were treated similarly to monitor complete death of non-transfectants. Two or three weeks after transfection only resistant colonies survived.

Supertransfection of the $K^k$ 4.1 clone with the $K^b$ gene

The clone $K^k4.1$ is a transfectant of D122 containing the $K^k$ gene and was selected with Geneticin (Gelber et al., Cancer Research 49 (1989), 2366–2373). For transfection of this clone with the $K^b$ gene another selective gene conferring resistance to the antibiotic hygromicin-B had to be used. The transfection protocol is the same as described above. $K^b$ plasmid (20 μg) and PSV2 hygro (2 μg) were transfected into $K^k4.1$ cells. Selection was performed in DMEM-10% FCS media containing 200 μg/ml hygromicin-B.

Supertransfection of the $K^d19.2$ clone with the $K^b$ gene

This clone is a transfectant of clone D122 containing the $K^d$ gene and was selected with Geneticin. The protocol is the same as described above.

Transfection of the DKM 25.1 clone with the $K^b$ gene

This clone is a transfectant of D122 containing the $K^b$ gene and was selected with Geneticin. The protocol is the same as described above.

EXAMPLE 5
Cytotoxicity assay in vitro and protection assays in vivo

C57BL/6, C3B6/F1, CB6/F1, B6D2/F1 and (BLXBM1)/F1 mice were immunized intraperitoneally three times at 7-day intervals with $2 \times 10^6$ cells, irradiated (5000 rad) and mitomycin treated (80 μg/ml/5–$10 \times 10^6$ for 1 hr at 37° C.).

For protection assays in vivo, 10 days after the last immunization mice were injected i.f.p. with $2 \times 10^5$ tumor cells or $5 \times 10^4$ tumor cells in 0.5 ml PBS via the tail vein (i.v.).

Spleen cells were taken 10 days after the last immunization and restimulated in vitro for 5 days with tumor cells (irradiated and mitomycin-treated as before) at a ratio of 20:1 (responders-stimulators) at a concentration of $4 \times 10^6$ spleen cells/ml in RPMI medium supplemented with 10% FCS, 0.4% combined antibiotics (penicillin and streptomycin), 2 mM glutamine, 1 mM sodium pyruvate, 1 mM nonessential amino acids, $2 \times 10^5$ β-mercaptoethanol and 1 mM Hepes, pH 7.4. The stimulated spleen cells were separated on lymphocyte preparation medium (Cedarlane Ontario), washed 3 times with PBS and suspended at a concentration $5 \times 10^6$ cells/ml.

Target labeling was performed with $^{35}$S methionine (NEN). 1–$2 \times 10^6$ target cells were starved for 2 hrs in DMEM 10% FCS without methionine and labeled for 6 hrs with 100 μCi of $^{35}$S-methionine. The cells were then washed 3 times with PBS and resuspended at $5 \times 10^4$ cells/ml. For incubation of labeled target cells with effector cells $5 \times 10^3$ labeled target cells/well (in 100 μl) were placed in U-shaped microplates (Nunc). Various numbers of effector spleen cells (in 100 μl) were incubated with the target cells for 5 hrs and 16 hrs at 37° C., 5% $CO_2$. The microplates were spun at 1000 rpm for 10 min and 100 μl aliquots of supernatant were taken into tubes for counting. The percentage of specific tumor cells lysis was calculated as follows:

$$\% \text{ lysis} = \frac{A - \text{Spontaneous release}}{\text{Maximal release} - \text{Spontaneous release}} \times 100$$

wherein A is the cpm of a certain well. Spontaneous release was determined by incubation of target cells with one volume of medium and maximal release was determined by incubation of target cells with one volume of 0.1M NaOH.

EXAMPLE 6
Transfection of H-2$K^b$+H-2$K^{bm1}$, H-2$K^b$+H-2$K^d$, H-2$K^b$+H-2$K^k$ into the highly metastatic clone D122

D122 was transfected with H-2$K^{bm1}$, H-2$K^d$ or H-2$K^k$ plasmid DNA as described in Example 4. All plasmids contained H-2K gene clones from genomic libraries of normal tissues and included 3.5–4.5 kb of 5' flanking region and 12 Kb of 3' flanking region. The H-2$K^b$ gene was derived from a cosmid library of placental DNA from a C57B1/10 mouse as a 10.5 Kb fragment containing eight exons, seven introns, 5' and 3' flanking regions and was recloned in pBR328.

Three weeks after transfection, 20 Gentamicin-resistant transfectants were isolated in the $K^b+K^k$ transfection. 30 Gentamicin-resistant transfectants were isolated in the $K^b+K^{bm1}$ transfection and only 10 Gentamicin-resistant transfectants were isolated in the $K^b+K^d$ transfection. The transfectants were analyzed for H-2$K^b$, H-2$K^{bm1}$, H-2$K^d$, and H-2$K^k$ expression by R.I.A. as described in Example 3 and FACS, using specific monoclonal antibodies to H-2$K^b$, H-2$K^{bm1}$, H-2$K^d$, and H-2$K^k$ cell surface glycoproteins as described in Example 2. The analysis showed 2 positive transfectants carrying both genes $K^b$ and $K^k$ (called Kk.b2 and Kk.b13), one positive transfectant carrying both genes $K^b$ and $K^d$ (called Kd.b5), and 4 positive transfectants carrying both genes $K^b$ and $K^{bm1}$ (called Kbm1.b4, Kbm1.b12, Kbm1.b14 and Kbm1.b19). Twelve clones transfected by pSV2-neo alone did not show any elevation of H-2K expression or change in the metastatic phenotype compared to the parental nontransfected cells (Plaksin et al., Proc. Natl. Acad. Sci. U.S.A. 85 (1988), 4463–4467). Since parallel transfection with 3 plasmids did not yield enough double H-2K expressor clones, a second transfection method was employed using clones previously transfected with H-2$K^d$, H-2$K^k$ or H-2$k^{bm1}$ and pSV2neo for supertransfection with H-2$K^b$ genes.

EXAMPLE 7
Transfection of H-2$K^b$ gene into the transfectants: $K^d19.2$, $K^k4.1$, and $K^{bm1}25.1$ The transfectants $K^d19.2$ ($K^d$/D122), $K^k4.1$ ($K^k$/D122), and $K^{bm1}$ 25.1 ($K^{bm1}$/D122) were transfected with the $K^b$ gene in order to get a large number of double transfectants. The hygromicin plasmid was cotransfected with the H-2$K^b$ gene. Three weeks after transfection 48 hygromicin-resistant transfectants were isolated in each group. The transfectants were analyzed for H-2K expression (according to the group) by R.I.A and FACS, using specific monoclonal anti-bodies to each haplotype. The analysis showed 30 positive transfectants in the $K^b/K^d19.2$ transfection. 6 transfectants were chosen for further analysis (called Kd.b24, Kd.b70, Kd.b80, Kd.b85, and Kd.b95). In the $K^b/K^k4.1$ transfection 28 positive clones were isolated, and 4 transfectants were chosen for further analysis (called Kk.b28, Kk.b72, Kk.b74, and Kk.b83). In the $K^b/K^{bm1}25.1$ transfection 10 positive clones were isolated. 2 transfectants therefrom were chosen for injection (called Kbm1.b7.1, and Kbm1.b68).

To test whether transfection by hygromicin had an effect on H-2 expression or metastatic phenotype, the hygromicin plasmid was transfected into the transfectants $K^d19.2$, $K^k4.1$ and $K^{bm1}25.1$. Three weeks after transfection 10 hygromicin-resistant transfectants were isolated in each group, 4 from each group were analyzed for cell surface expression by the R.I.A method described in Example 3. There was no change in H-2K or H-2D class I antigens compared to the parental transfectants ($K^d19.2$, $K^k4.1$, $K^{bm1}25.1$).

EXAMPLE 8
Analysis of cell surface expression

Analysis of cell surface expression was performed using the Fluorescence Activated Cell Sorter (FACS) and the R.I.A (see Examples 2 and 3). For both methods the same monoclonal antibodies were used.

In the $K^b$, $K^d$/D122 transfection the antibodies that were used were: K-10-18-9 ($\alpha K^d$), K-9-178 ($\alpha K^b$), and 28-14-8 ($\alpha D^b$).

In the $K^b$,$K^k$/D122 transfection the antibodies were: 16-3-1 ($\alpha K^k$), 20-8-4 ($\alpha K^b$), and 28-14-8 ($\alpha D^b$).

In the $K^b$,$K^{bm1}$/D122 transfection the antibodies were K-9-178 ($\alpha K^b$, not cross-re active with $K^{bm1}$), 20-8-4 (can bind both $K^b$ and $K^{bm1}$), and 28-14-8 ($\alpha D^b$) $K^{bm1}$ levels were calculated by the difference between binding of antibodies 20-8-4 and K-9-178:

$$\text{Results in the control clone } X = \frac{20\text{-}8\text{-}4}{K\text{-}9\text{-}178}$$

all binding above (X) x (K-9-178) in the transfectants is the binding to the $K^{bm1}$ class I antigens.

Table 1 shows the results of one of the R.I.As carried out with D122, $K^b$/D122 (transfectants are called $K^b$77.8 and $K^b$39.5), $K^d$/D122 (transfectant is called $K^d$19.2) and the clones from $K^b$/$K^d$/D122 transfections that were prepared as described in Examples 6 and 7 (transfectants are called Kd.b24, Kd.b70, Kd.b75, Kd.b80, Kd.b85, Kd.b95 and Kd.b5). The combined results of at least six R.I.As performed at different times, indicate that all the double transfectants were highly positive in $K^d$ class I MHC antigen in relation to D122, and were moderately positive in the $K^b$ bclass I MHC antigen.

The double transfectants were moderately positive in the $K^b$ class I MHC antigen in relation to $K^d$19.2 and they were highly positive in the $K^d$ class I MHC antigen in relation to $K^b$ 77.8 and $K^b$ 39.5.

Among the double transfectants, the two transfectants exhibiting the highest expression of both class I MHC antigens ($K^b$ and $K^d$) were termed Kd.b85 and Kd.b95.

The H-2$D^b$ expression of all the transfectants and the parental D122 was more or less the same.

Table 2 shows the results of one of the R.I.As performed with D122, $K^b$/D122 transfectants (called $K^b$77.8 and $K^b$39.5), $K^k$/D122 (transfectant is called $K^k$4.1) and the clones from $K^b$,$K^k$/D122 (transfectants are called Kk.b2, Kk.b28, Kk.b72, Kk.b74 and Kk.b83). The combined results of at least six R.I.As carried out at different times indicate that all the double transfectants were highly positive in the $K^k$ class I MHC antigen in relation to D122 except Kk.b2 and Kk.b13 that are moderately positive (these transfectants were obtained with the method described in Example 6).

The double transfectants were moderately positive in the expression of $K^b$ antigen in relation to D122 (Kk.b2 exhibited the highest expression). In relation to $K^k$4.1 cells the double transfectants were moderately positive in the $K^b$ class I MHC antigen expression and the amount of the H-2$K^k$ antigen expressed was similar to $K^k$4.1 for most supertransfected clones. Kk.b83 expressed about 50% density of the H-2$K^k$ molecules in relation to $K^k$4.1 cells.

K-2 and K-13 show a low density of the H-2$K^k$ antigen expression.

In relation to the $K^b$/D122 transfectants the double transfectants were highly positive in H-2$K^k$ (Kk.b2 and Kk.b13 were moderately positive) and were about the same as $K^b$77.8 and less than $K^b$39.5 in the H-2$K^b$ expression. The H-2 $D^b$ expression of all the transfectants was lower than that of the parental clone D122 ($K^k$.b74 and Kk.b83 were about twofold lower than in parental cells).

Table 3 shows the results of one of the R.I.As carried out with D122, $K^b$/D122 (transfectants are called $k^b$77.8 and $K^b$39.5), $K^{bm1}$/D122 (transfectant is called $K^b$25.1) and $K^b$, $K^{bm1}$/D122 transfectants obtained with the method described in Examples 4 and 5 (transfectants are called Kbm1.b4, Kbm1.b7.1, Kbm1.b12, Kbm1.b68, Kbm1.b14, and Kbm1.b19). The combined results of at least 6 different R.I.As performed at different times indicate that all the double transfectants were positive in H-2$K^{bm1}$ expression in relation to D122 (Kbm1.b68 was very highly positive) and were also positive in H-2$K^b$ expression in relation to the parent D122 (Kbm1.b68 was the one with the highest expression).

In relation to $K^b$/D122 transfectants, the double transfectants were similar in expression to $K^b$77.8 but lower than $K^b$39.5.

In relation to $K^{bm1}$/D122 ($K^{bm1}$25.1), the double transfectants expressed 2–4 times as much H-2$K^b$ antigen. The H-2$K^{bm1}$ expression of the double transfectant Kbm1.b7.1 was about the same as that of $K^{bm1}$25.1, Kbm1.b4 and Kbm1.b12 expressed a little less of this antigen, Kbm1.b14 and Kbm1.b19 expressed 5 times less molecules than $K^{bm1}$25.1 and Kbm1.b68 was highly positive (about 8 times more than $K^{bm1}$25.1 and Kbm1.b68 was highly positive (about 8 times more than $K^{bm1}$25.1). With respect to the H-2$D^b$ expression all the transfectants and the parental D122 showed more or less the same level. FACS analysis of D122 and transfectants was repeatedly performed and the results showed consistency with the R.I.A results.

EXAMPLE 9

Analysis of genomic DNA

Transfected genes are usually inserted randomly into the genome. To compare the copy number of the various H-2K genes inserted in the various transfections into the genome genomic DNA of all the clones from each type of transfection was prepared. DNAs were restricted with restriction enzymes which were chosen depending on the H-2K gene inserted (EcoRI for H-2$K^b$ and H-2$K^{bm1}$, SalI for H-2$K^k$ and HindIII for H-2$K^d$), electrophoresed and hybridized in the gel to 30-mer oligo-nucleotides which were also chosen depending on the type of transfectants.

Figure 1A:
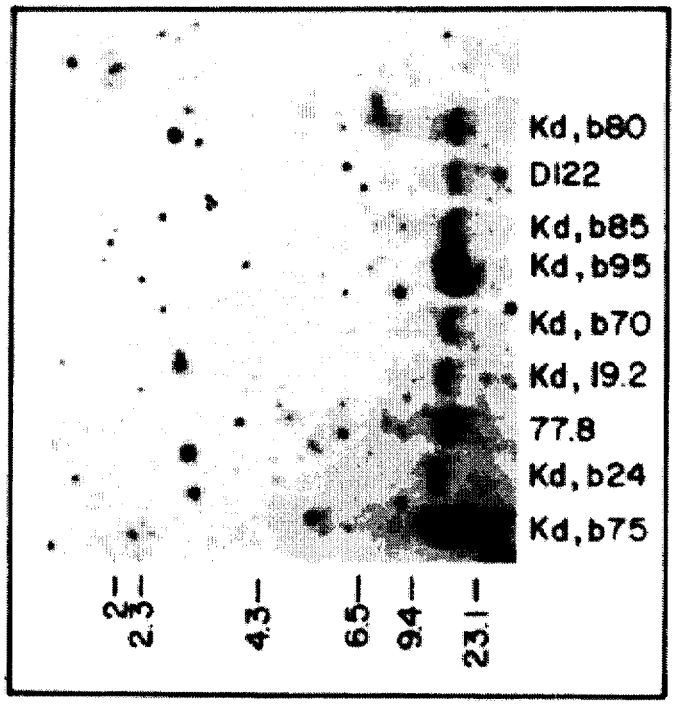
FIGS. 1a and b Genomic DNA analysis of D122, $K^b77.8$, $K^d19.2$, and $K^b,K^d/D122$ transfectants. Restriction of DNAs was performed with EcoRI (a) and HindIII (b). Restricted DNAs were electrophoresed and hybridized in the gel to end labeled 30-mer $K^b$ specific oligonucleotide (a) and to end labeled 30-mer $K^d$ specific oligonucleotide (b). Gels were washed in 0.5×SSC at 54° C. and autoradiography was performed for 12 hrs. λ-DNA digested with HindIII was used as a molecular weight marker.

The results for the $K^b$,$K^d$/D122 transfections are shown in FIG. 1.

Figure 1B:
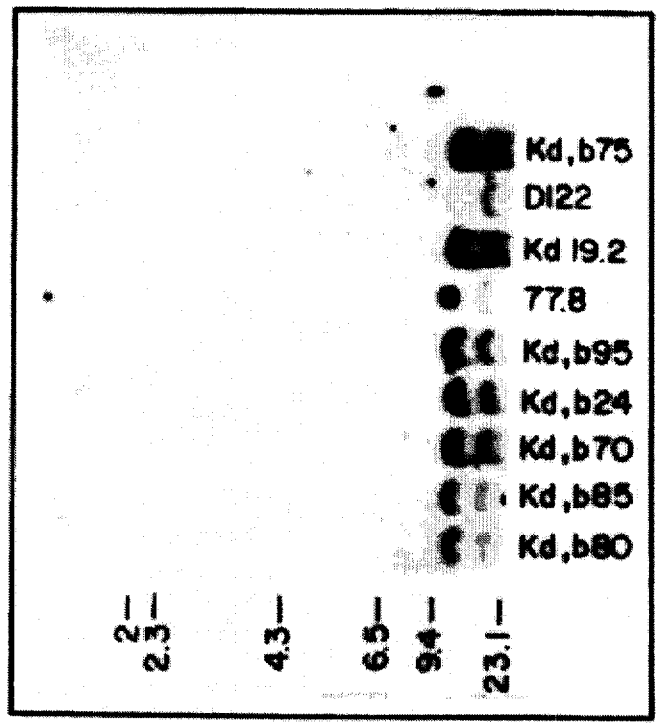

In the parental D122 (FIG. 8a) the double copy fragment of the endogenous H-2$K^b$ gene can be clearly seen. EcoRI does not cut in the H-2$K^b$ gene but releases a 10.5 Kbp fragment that contains the gene. Densitometric analysis shows that the double transfectant Kd.b75 contains five times the copy number of D122 (10 copies), the double transfectant Kd.b95 contains 6 times the copy number of D122, the other double transfectants Kd.b24, Kd.b85, Kd.b80, and Kd.b70 contain 1.5–2 times the copy number of D122, the $K^b$/D122 transfectant $K^b$77.8 has 3 times the copy number of D122 and the $K^d$/D122 transfectant $K^d$19.2 has the same copy number as D122. FIG. 1b shows the same DNAs cut with HindIII and hybridized to a $K^d$ probe. The 10.5 Kbp HindIII fragment of the double transfectants Kd.b80, Kd.b85, Kd.b70, Kd.b24, Kd.b95, Kd.b75, and the $K^d$/D122 transfectant $K^d$19.2 represents the insertion of the H-2$K^d$ gene into the genomic DNA (the upper band). There is no hybridization at all with the parental D122 or with the $K^b$/D122 transfectant $K^b$77.8 DNAs. The higher M.W. band probably represents a cross-hybridization with the H-2$K^b$ gene, as can be seen from the hybridization to DNAs of D122 and $K^b$77.8.

FIG. 2 shows the results of the $K^b$,$K^k$/D122 transfections.

Figure 2A:
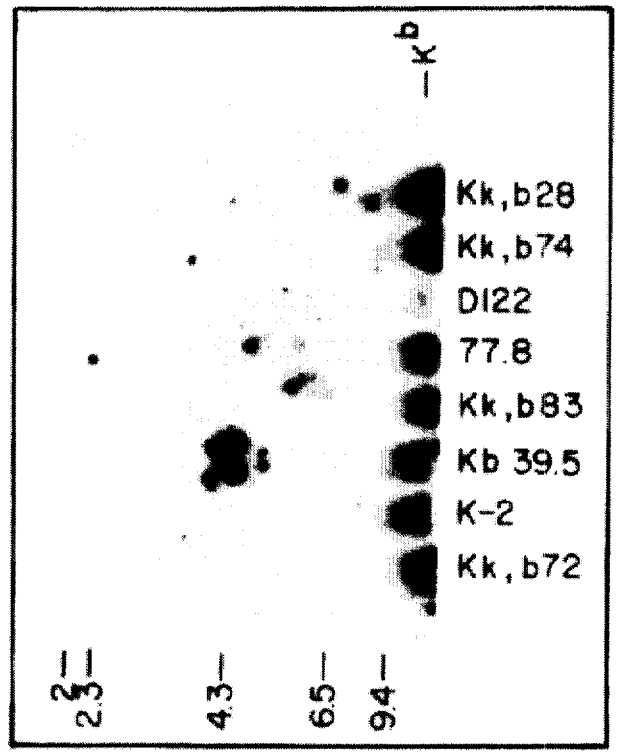
FIGS. 2a and b Genomic DNA analysis of D122, $K^b77.8$, $K^b39.5$, $K^k4.1$, and $K^b,K^k/D122$ transfectants. Restriction of DNAs was performed with EcoRI (a) and HindIII (b). Restricted DNAs were electrophoresed and hybridized in the gel to end labeled 30-mer $K^b$ specific oligonucleotide (a) and to end labeled 30-mer $K^d$ specific oligonucleotide (b). Gels were washed in 0.5×SSC at 54° C. and autoradiography was performed for 12 hrs. λ-DNA digested with HindIII was used as a marker.

FIG. 2a (DNA cut with EcoRI) shows that there is a high copy number of inserted $K^b$ genes in the double transfectants (Kk.b72, K-2, Kk.b83, Kk.b74, Kk.b28), and in the $K^k$/D122 transfectants ($K^b$39.5 and $K^b$77.8) as compared to D122 cells.

Figure 2B:
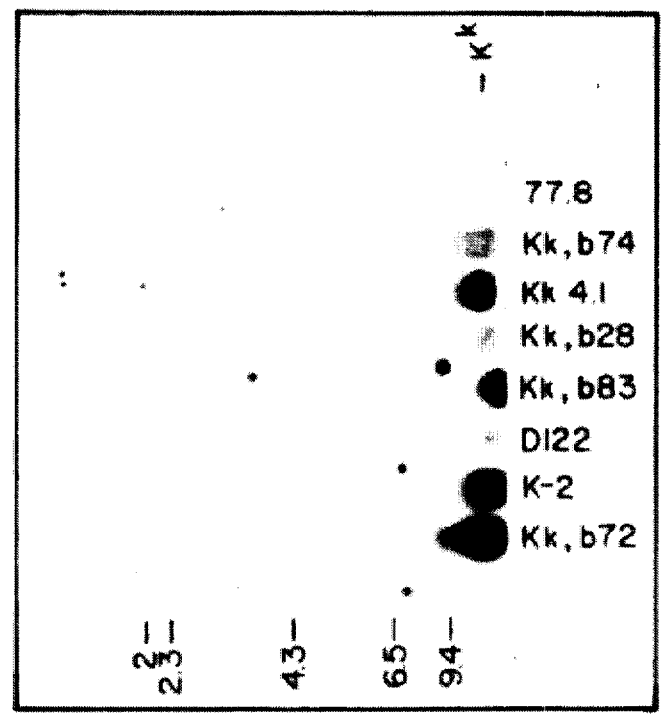

FIG. 2b (DNA cut with SalI) shows that there is a high copy number of the $H_2K^k$ gene in the double transfectants (Kk.b72, K-2, and Kk.b83), and in the $K^k$/D122 transfectant ($K^k$4.1), and a low copy number in Kk.b28 and Kkb74. A faint signal is also observed with DNAs of D122 and $K^b$77.8 that do not contain $H_2K^k$ genes, due to a slight cross-hybridization.

FIG. 3 shows the results of the $K^b,K^{bm1}$/D122 transfections.

Figure 3A:
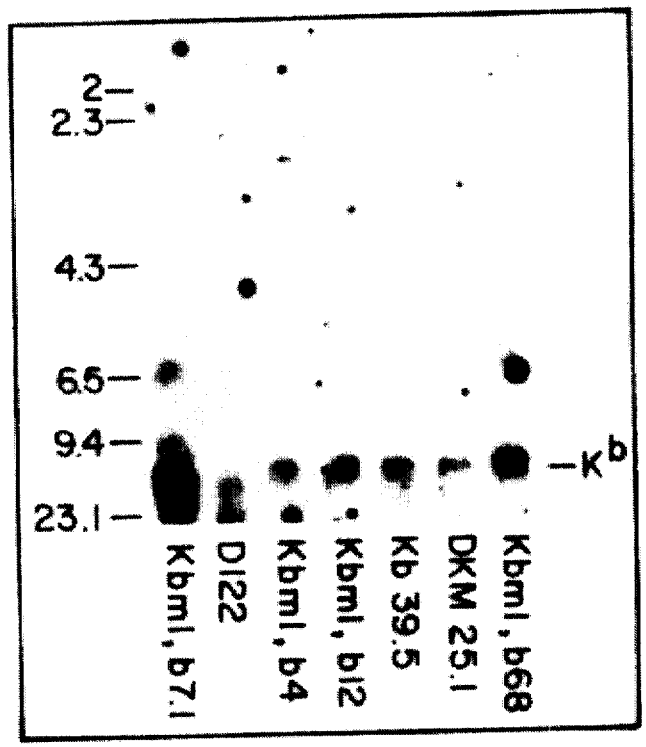
FIGS. 3a and b Genomic DNA analysis of D122, $K^{bm1}25.1$ (DKM 25.1), $K^b39.5$, and $K^b,K^{bm1}/D122$ transfectants. Restriction of DNAs was performed with EcoRI (a) and HindIII (b). Restricted DNAs were electrophoresed and hybridized in the gel to end labeled 30-mer $K^b$ specific oligonucleotide (a) and to end labeled 30-mer $K^d$ specific oligonucleotide (b). Gels were washed in 0.5×SSC at 54° C. and autoradiography was performed for 12 hrs. λ-DNA digested with HindIII was used as a marker. $K^{bm1}25.1$ is named DKM25.1 in the figure.

FIG. 3a shows the 10.5 Kb EcoRI fragments that represent both endogenous and transfected $H-2K^b$ genes. Densitometric analysis shows that the double transfectant Kbm1,b7.1 contains 9 times the copy number of D122 and $K^{bm1}$25.1 ($K^{bm1}$ transfectant), the transfectant Kbm1,b68 contains 5 times the copy number of D122, the transfectant Kbm1,b12 contains 4 times the copy number and the double transfectant Kbm1,b4 and the $K^b$ transfectant $K^b$39.5 carry 1.5–2 times the copy number of D122.

Figure 3B:
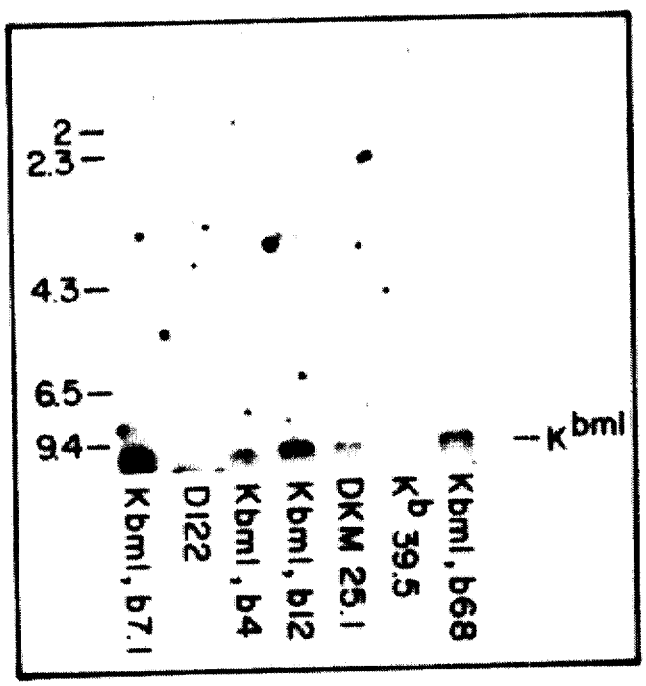

FIG. 3b (DNA cut with EcoRI) shows that all the double transfectants (Kbm1,b7.1, Kbm1,b4, Kbm1, b12, Kbm1, b68), and the $K^{bm1}$ transfectant $K^{bm1}$25.1 contain the inserted gene $H-2K^{bm1}$, while D122 and $K^b$39.5 do not show hybridization with the $K^{bm1}$ probe. Although the highest copy number was observed in the clone Kbm1,b7.1, the highest expression was monitored in Kbm1,b68 (see Table 3).

EXAMPLE 10

Tumorigenicity and metastatic behavior of the double transfectants in homozygous mice (C57BL/6)

Growth and metastatic potential of the double transfectants of D122 was investigated in vivo. The transfectants were grown in tissue culture (in gentamicin or hygromicin selection medium, depending on the type of transfection) and injected into C57BL/6 mice, which are the original hosts of the tumor. Cells were injected i.f.p. to evaluate growth rate and spontaneous metastasis, and intravenously to evaluate experimental metastasis (see Example 1). Parental highly metastatic D122 cells $K^b$/D122 transfectants ($K^b$39.5 and $K^b$77.8) and single transfectants $K^d$19.2, $K^k$4.1, $K^{bm1}$25.1 were used as controls.

$K^b,K^d$/D122 transfectants in C57BL/6 mice

Figure 4:
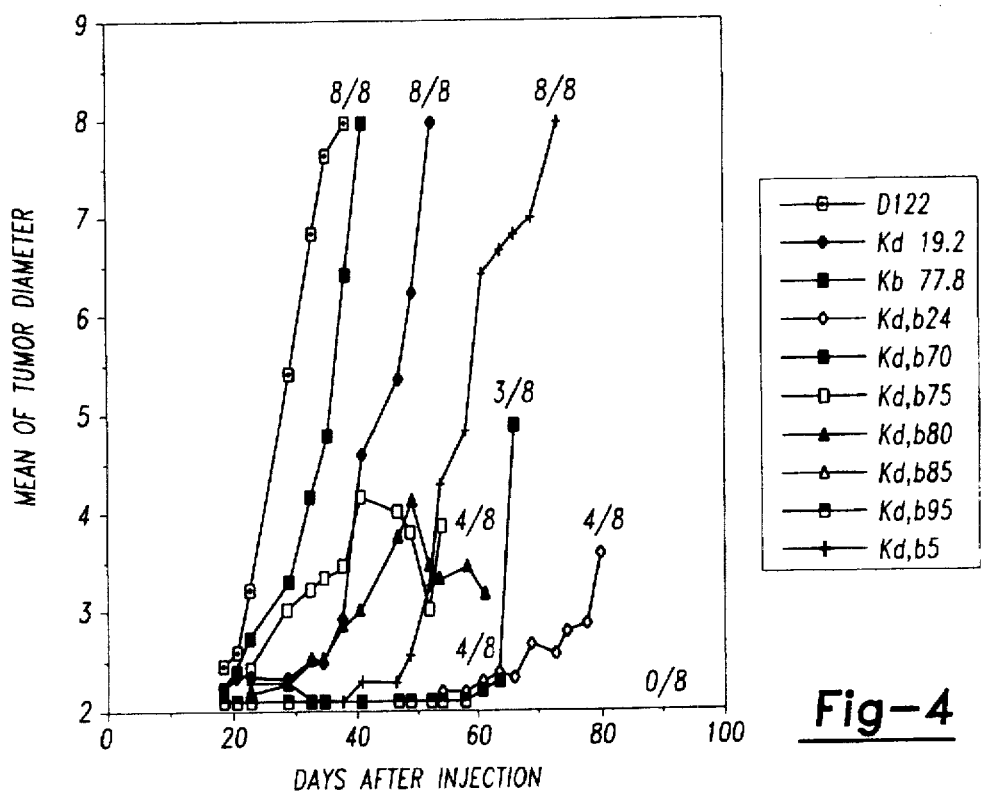
FIG. 4: Growth curves of D122, $K^b77.8$, $K^d19.2$, and $K^b,K^d$ transfectants in C57BL/6 mice. C57BL/6 mice were injected i.f.p. with $2 \times 10^5$ cells/mouse and growth rate was measured as described in Example 10. Tumor size is expressed by diameter of the tumor-bearing foot pad. The transfectants Kd,b85 and Kd,b95 did not grow at all (0/8). Numbers in the figure indicate the fraction of mice that grew tumors.

FIG. 4 shows the growth curves of the tumors injected in one of the three i.f.p. experiments performed. D122 and the single transfectant $K^b$77.8 grew fast. The single allogeneic transfectant $K^d$19.2 showed an initial retardation but regained fast growth. On the other hand, the 7 positive transfectants grew slowly or did not grow at all. The double transfectants Kd.b85 and Kd.b95 did not grow in any of the injected mice. In the double transfectant Kd.b5 all the mice were amputated (see Example 1), but the growth of the tumor was very slow, the last mouse was amputated only 75 days after injection. With the other double transfectants (Kd.b24, Kd.b70, Kd.b75, and Kd.b80) the tumors did not grow at all in about half of the mice. D122-neo and $K^d$19.2-hygro grew like the parental D122 or parental $K^d$19.2, respectively (data not shown).

Mice were sacrificed 30 days after amputation, their lungs were excised and metastatic load was evaluated as described in Example 1. Table 4 summarizes the results of the i.f.p. experiments. The parental D122 was highly metastatic, while the transfectants, either single transfectants or double transfectants, were low or non-metastatic. Experimental metastasis was tested by i.v. injection in three independent experiments. Mice were sacrificed when the control group (injected with the parental D122) died, generally 35–39 days after injection. The results of the three experiments were consistent. Table 4 summarizes the results of two i.v. experiments. The results are consistent with the results of the i.f.p. experiments. The parental D122 was highly metastatic while the double and the single transfectants were low or non-metastatic. Survival experiments were performed to test whether the reduction of the metastatic phenotype is time-dependent or absolute. In one of the three i.v. experiments the double transfectants Kd.b95 and Kd.b85 and the single transfectants were not sacrificed when the control group (D122) died from metastasis after 35 days, but the survival of mice was monitored. The single transfectants $K^b$77.8 and $K^d$19.2 died from metastasis after 45–50 days. In contrast thereto the double transfectants were free of metastases 120 days after injection (data not shown). These results indicate that the reduction of the metastatic phenotype in the single transfectants is time-dependent and in the double transfectants is absolute.

$K^b,K^k$/D122 transfectants in C57BL/6 mice

Figure 5:
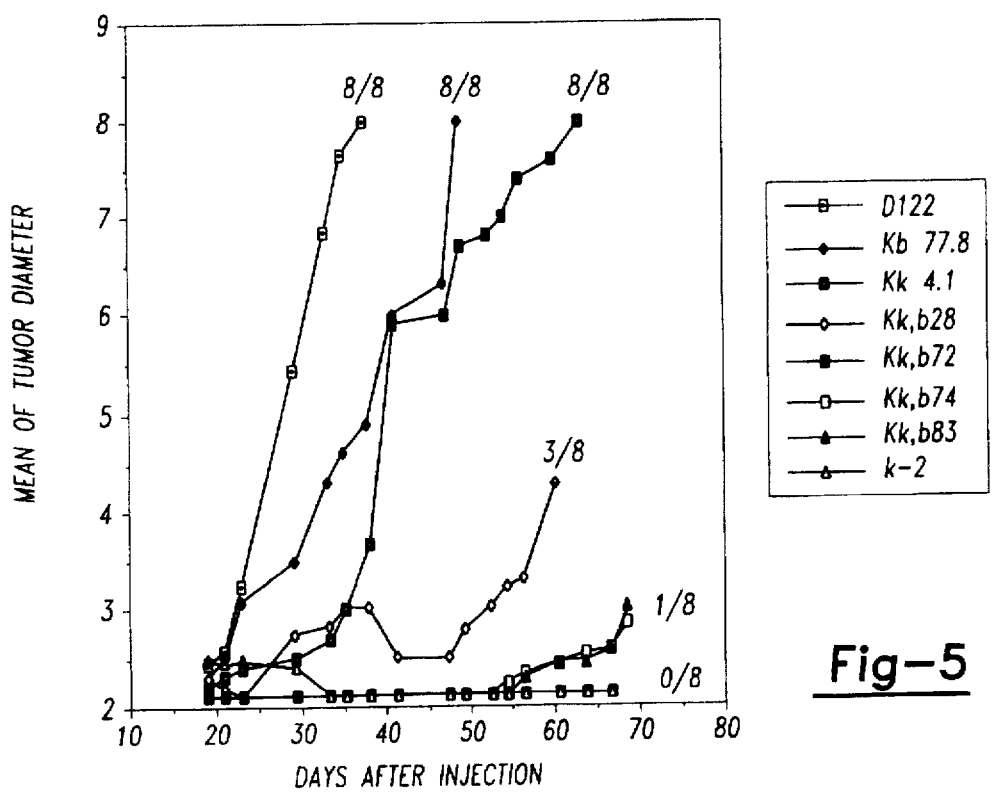
FIG. 5: Growth curves of D122, $K^b77.8$, $K^k4.1$, and $K^b,K^k$ transfectants in C57BL/6 mice. C57BL/6 mice were injected i.f.p. with $2 \times 10^5$ cells/mouse and growth rate was measured as described in Example 10. Tumor size is expressed by diameter of the tumor-bearing foot pad. The transfectants Kk,b72 and K-2 did not grow at all (0/8).

FIG. 5 shows the growth curves of the tumors injected in one out of three i.f.p. experiments performed. In all three experiments, the parental D122 cells grew faster than the transfectants (the single transfectants and the double transfectants) and the single transfectants, including $K^k$4.1 grew faster than the double transfectants. With the double transfectant Kk.b28 tumors in only 3 out of 8 mice grew, and with the other double transfectants primary tumors did not grow in nearly all the mice: With the transfectants Kk.b74 and Kk.b83 1/8 of the mice grew tumors and with the transfectants Kk.b72 and K-2 none of the mice grew tumors.

Mice were sacrificed 30–35 days after amputation, their lungs were excised and metastatic load was evaluated. Table 5 summarizes the results of two independent i.f.p. experiments. The parental D122 was cloned highly metastatic, the single transfectants $K^b$77.8 and $K^d$19.2 were non-metastatic. Most mice inoculated with the double transfectants did not grow primary tumors. In the group inoculated with the double transfectants Kk.b28, the primary tumor grew in 3 out of 8 mice but their lungs were free from metastases.

Experimental metastasis was tested by i.v. injection in three independent experiments. Mice were sacrificed at the time of death of the control group (mice injected with D122), generally 30 days after injection. Table 5 summarizes the results of two i.v. experiments. Again the parental D122 was highly metastatic, the single transfectants were non-metastatic and the double transfectants tested (K.kb72 and K-2) were also non-metastatic.

$K^b,K^{bm1}$/D122 transfectants in C57BL/6 mice

FIG. 6 shows the growth curves of the $K^bmK^{bm1}$/D122 clones injected in one of the four i.f.p. experiments performed. Again in all four experiments D122 and the single transfectants ($K^b$77.8 and $K^{bm1}$25.1) grew faster than the four double transfectants (Kbm1,b4, Kbm1,b12, Kbm1,b7.1 and Kbm1,b68). In the groups inoculated with the double transfectants Kbm1,b68 and Kbm1,b7.1 4 out of 8 mice did not grow at all. The mice inoculated with other double transfectants grew tumors very slowly: In the group injected with the transfectants Kbm1,b4 and Kbm1,b12 the last mouse was amputated on day 78 and 96, respectively, while in the group injected with the parental D122 and the single transfectants the last mouse was amputated 30–40 days after injection.

Mice were sacrificed 30 days after amputation, their lungs were excised and metastatic load was evaluated. Table 6 summarizes the results of i.f.p. experiments with the $K^b,K^{bm1}$/D122 transfectants. D122 was highly metastatic, the single and the double transfectants were non-metastatic.

Additional transfectants (not shown) that grew very slowly (the last mouse was amputated after 110 days), did show a moderate metastatic phenotype (spontaneous metastases). RNA analysis of cells derived from these metastases showed that those transfectants had lost the expression of the transfected genes.

Table 6 also shows the results of tests for experimental metastasis. Experimental metastases were tested by i.v. injection in five independent experiments. Mice were sacrificed at the time of death of the control group (D122), 40 days after injection. The results were the same as with the i.f.p. experiments: The parental D122 was highly metastatic, the single and the double transfectants were non-metastatic.

Thus it can be seen that in all types of transfections the single and the double transfectants were non-metastatic both in i.v. and i.f.p. experiments, while the parental D122 clone was highly metastatic in all cases.

The major difference between the single and the double transfectants was observed in their growth patterns and the growth rates of the tumors. The single transfectants grew faster than the double transfectants in all types of transfection. Moreover, many double transfectants (Kd.b85, Kd.b95, Kk.b72, Kk.b74, Kkb83 and K-2) did not grow at all and in other double transfectants the primary tumors grew only in a part of the mice. only in 3 out of 16 double transfectants (K.db5, Kbm1.b12, and Kbm1.b4) the tumors grew in all the mice injected but the growth rates in those mice were very slow as compared to the single transfectants.

EXAMPLE 11
Tumorigenicity and metastatic behavior of the double transfectants in F1 matched mice The double transfected clones as described in Example 10 were grown in tissue culture and injected into F1 matched mice. Thus, $K^b,K^d$/D122 cells were tested in (Balb/cxC57BL/6)F1 (H-$2^d$×H-$2^b$) mice, (designated CB6/F1), $K^b,K^k$/D122 cells were tested in (C3HxC57VL/6)F1 (H-$2^k$× H-$2^b$) mice (designated C3B6/F1) and $K^b,K^{bm1}$/D122 cells were tested in (B6.CH2.bm1×C57B1/6)F1 (H-$2^{bm1}$×H-$2^b$) mice (designated (BL×BM1)F1). Cells were injected intrafootpad to evaluate growth rate and spontaneous metastasis formation, and intravenously to evaluate experimental metastasis (see Example 1).

$K^b,K^d$/D122 transfectants in CB6/F1 mice

FIG. 7 shows the growth curves of the tumors injected in one of two i.f.p. experiments performed. In both experiments D122 and the single transfectants ($K^b$77.8 and $K^d$19.2) grew faster than the double transfectants. The double transfectants Kd.b24 and Kd.b75 did not grow at all in the CB6/F1 mice, and in the group injected with the other double transfectants the primary tumor grew in part of the mice (Kd.b70-5/8, Kd.b80-6/8, Kd.b85-4/8 and Kd.b95-3/8). The single transfectants $K^d$19.2 grew slower than both D122 and $K^b$77.8 (with $K^d$19.2 the last mouse was amputated 50 days after injection, whereas with D122 and with $K^b$77.8 the last mouse was amputated 35 days after injection).

Mice were sacrificed 30 days after amputation, their lungs were excised and metastatic load was evaluated. Table 7 summarizes the results of two independent i.f.p. experiments. The parental D122 and the single transfectants were highly metastatic, while the double transfectants that grew were non-metastatic.

Experimental metastasis was tested by i.v. injection in two independent experiments. Mice were sacrificed at the time of death of the control group (parental D122), generally 30 days after injection. The results were comparable to those of the i.f.p. experiments. The parental D122 and the single transfectants were highly metastatic. The double transfectants, in contrast, were non-metastatic.

$K^b,K^k$/D122 transfectants in C3B6/F1 mice

FIG. 8 shows the growth curves of tumors injected in one of two i.f.p. experiments performed. Again the parental D122 and the single transfectants ($K^b$77.8 and $K^k$4.1) grew faster than the double transfectants. Three out of four double transfectants did not grow at all, and in the only double transfectant that grew (Kk.b74) the primary tumor grew only in 3 out of 8 mice. The single transfectant $K^b$77.8 grew even faster than the parental D122 in this particular experiment. However, in most experiments $K^b$77.8 grew at a rate similar to that of the D122 tumors.

Mice were sacrificed 30 days after amputation, their lungs were excised and metastatic load was evaluated. Table 8 summarizes the results of two independent i.f.p. experiments. Again in this strain of F1 mice the single transfectants and the parental D122 were highly metastatic and the only double transfectant that grew, Kkb74 (3/8 mice), was non-metastatic.

The i.v. experiments gave the same results. Experimental metastasis was tested by i.v. injection in two independent i.v. experiments. Mice were sacrificed at the time of death of D122 injected mice which occurred 35 days after injection. The single transfectants and the parental D122 were highly metastatic, and all the double transfectants were low or non-metastatic.

$K^b,K^{bm1}$/D122 transfectants in (BL×BM1)/F1 mice

FIG. 9 shows the growth curves of the tumors injected in one of two i.f.p. experiments performed. In contrast to the transfections described above in this experiment, all the clones, i.e. the parental D122, the single transfectants ($K^b$77.8 and $K^{bm1}$25.1) and the double transfectants (except Kbm1.b68) grew progressively in F1 mice. In the group injected with the double transfectant Kbm1.b68 the primary tumor grew in only 4 out of 8 mice.

Mice were sacrificed 30 days after amputation, their lungs were excised and the metastatic load was evaluated. Table 9 summarizes the results of two i.f.p. experiments. The results were similar to the previous types of transfections. The parental D122 and the single transfectants were highly metastatic while the double transfectants were non-metastatic.

To summarize, it can be concluded that in all types of transfectants, excluding $K^b,K^{bm1}$/D122 transfectants, the parental D122 and the single transfectants grew faster than the double transfectants in F1 matched mice and in C57BL mice. Some of the double transfectants (Kd.b24, Kd.b75, K-2, Kk.b72, and Kk.b83) did not grow at all in F1 matched mice.

The major difference between the metastatic behavior of single transfectants and double transfectants is observed in F1 mice as compared to C57BL/6 mice. In the F1 mice the single transfectants were metastatic like the parental D122 and the double transfectants were non-metastatic, while in C57BL mice both single and double transfectants were non-metastatic, both in spontaneous and experimental metastasis experiments.

EXAMPLE 12
Immunogenicity of the double transfectants

To test in vivo whether the low metastatic phenotype of the double transfectants is the result of an interaction with the T-cell dependent immune system of the host, i.f.p. injection experiments were performed in nude mice, which are deficient in thymus dependent mature T cells.

FIG. 10, FIG. 11 and FIG. 12 show the growth curves of the $K^b,K^d$/D122, $K^b,K^k$/D122, and $K^b,K^{bm1}$/D122 transfectants in nude mice, respectively. The growth rates of all the double transfectants in the various gene combinations were similar to the growth rates of the parental D122 and the single transfectants in the nude mice.

Mice were sacrificed 30 days after amputation, their lungs were excised and metastatic load was evaluated. Table 10 summarizes the results of three independent i.f.p. experiments. All clones, the parental D122, the single transfectants and the double transfectants were highly metastatic. From these results it may be concluded that the low metastatic phenotype of the double transfectants is the result of their elevated immunogenicity which is dependent on the interaction with mature T cells of the host.

EXAMPLE 13
Protection experiments in C57BL/6 mice

The results, so far, indicated that double transfectants show a reduced tumorigenicity in C57BL/6 recipients compared to single transfectants that carry a single H-2K$^b$ gene or allogeneic (H-2K$^d$, H-2K$^k$, H-2K$^{bm1}$) genes. Both single and double transfectants were non-metastatic in C57BL/6 mice.

It was therefore tested whether the increased immunogenicity of the double transfectants could protect the host from metastasis generated by the parental D122 cells, or affect the growth rates of the single transfectants.

Mice were immunized three times intraperitoneally at 7-day intervals with 2×10$^6$ tissue culture grown cells, irradiated at 5000 rad and treated with 80 µg/ml mitomycin C for 1 hr. Seven days after the third injection the mice were challenged i.f.p. with 2×10$^5$ or i.v. with 5×10$^5$ living tumor cells.

Immunization with the double transfectants had no effect on the growth rates of the syngeneic single transfectant (K$^b$77.8) or the parental D122 cells, but completely abolished the growth of the matched allogeneic single transfectants K$^d$19.2 in mice immunized with Kd.b85 or Kd.b95 and K$^k$4.1 in mice immunized with K-2 or Kk.b72. Immunization with single allogeneic transfectants completely abolished the growth of the same single allogeneic transfectants, but did not affect the growth of the parental D122 cells or the syngeneic single transfectant K$^b$77.8. Immunization with the syngeneic single transfectant K$^b$77.8 had no effect on the growth rates of the single transfectants or parental D122 cells. However, major effects were observed on the metastatic spread of D122 parental cells in immunized mice. Table 11 summarizes the results of i.v. and i.f.p. challenges with D122 cells. Mice were immunized with D122, single transfectants (K$^b$77.8 and K$^d$19.2) and double transfectants (Kd.b85 and Kd.b95) and challenged i.v. and i.f.p. with the parental D122 cells. In both modes of challenge, the mice immunized with K$^d$19.2 and mice immunized with D122 were highly metastatic. Statistical analysis showed no difference between metastases in the control group and metastases in mice immunized with the parental D122 cells or mice immunized with K$^d$19.2 both in i.v. and i.f.p. challenges. Mice immunized with K$^b$ 77.8 were moderate metastatic (although there were no statistical differences from the control group, see p values in Table 11). Tumors in mice immunized with the double transfectants were not metastatic.

Table 12 summarizes the results of i.v. and i.f.p. challenge experiments performed in mice immunized as described above using the K$^b$.K$^k$/D122 transfectants as immunizing agents. In the group challenged i.f.p. with D122 cells, mice were sacrificed 30 days after amputation, their lungs were excised and metastatic load was evaluated. The control group of mice immunized with the parental D122 and mice immunized with K$^k$4.1 were highly metastatic. Mice immunized with K$^b$77.8 showed moderate metastasis formation, although there were no statistical differences to the control group (see p values, Table 12). On the other hand, mice immunized with the double transfectants (K-2 and Kk.b72) were non-metastatic.

Experimental metastases in mice immunized with D122, K$^b$77.8, K$^k$4.1, K-2 and Kk.B72 were tested by i.v. injection of D122 cells. Mice were sacrificed at the time of death of the control group (mice that were not immunized), i.e., 30 days after injection. Mice in the control group and mice immunized with the parental D122 were highly metastatic, and mice immunized with the single transfectants K$^b$77.8 and K$^k$4.1 were moderately metastatic. There was no statistical difference between mice immunized with K$^b$77.8 and the control group, but there was a difference between the group immunized with K$^k$4.1 and the control group; see p values in Table 12. In contrast, all mice immunized with the double transfectants were non-metastatic. The results of protection experiments with the K$^b$.K$^{bm1}$/D122 transfectants in C57BL/6 mice are consistent with the results of the other two types of transfections.

The foregoing results can be summarized as follows:
(1) Immunization with the inactivated parental D122 cells did not significantly reduce the metastatic spread of the non-inactivated D122 cells with which mice were challenged.
(2) Immunization with the syngeneic single transfectant K$^b$77.8 caused reduction in the metastatic spread of D122 cells in the immunized recipients (tumors were moderately metastatic).
(3) Immunization with the double transfectants caused total abolishment of D122 derived metastases in the immunized recipients.
(4) Immunization with the double transfectants or the single allogeneic transfectants had no effect on the growth rates of the local D122 cells or of the local syngeneic single transfectants but completely abolished the growth of the allogeneic single transfectants as local tumors.
(5) Immunization with the syngeneic single transfectant K$^b$77.8 had no effect on the growth rates of D122 cells or of single transfectants.
(6) Immunization with the allogeneic single transfectant K$^k$4.1 caused moderate reduction in the metastatic spread of the D122 cells which were injected as an i.v. challenge; however, another allogeneic single transfectant (K$^d$19.2) did not have a similar effect.

EXAMPLE 14
Protection experiments in F1 mice

Protection experiments in C57BL/6 mice showed-that the co-expression of the H-2K$^b$ gene with an allogenic H-2K gene increased the immunogenicity of these cells and afforded the mice protection against metastatic spread of parental D122 cells. Subsequently it was tested whether in F1 mice the expression of two H-2K genes syngeneic to the recipient MHC class I on tumor cells would also afford better protection against metastatic cells. F1 matched mice were immunized by three intraperitoneal injections of 2×10$^6$ tissue culture grown cells, irradiated at 5000 Rad and treated with 80 µg/ml mitomycin-C for 1 hr. given at 7-day intervals. Seven days after the third immunization, the F1 mice were challenged i.f.p. with 2×10$^5$ or i.v. with 5×10$^4$ living D122 parental tumor cells. Table 13 summarizes the results of the metastatic behavior of D122 cells injected i.v. and i.f.p. into B6D2/F1 mice (H-2$^b$, H-2$^d$) previously immunized with D122, single transfectants and double transfectants (K$^b$.K$^d$/D122 transfectants).

There was no difference in the growth rates between the control group (non-immunized) and the immunized mice with respect to all clones tested (data not shown). Spontaneous metastases were evaluated in i.f.p. challenged mice, 30 days after amputation of the primary tumors, and experimental metastases were evaluated in i.v. challenged mice that were sacrificed at the day the control group (non-immunized recipients) died. In both types of challenge the control group, mice immunized with parental D122 cells, and mice immunized with the single transfectants ($K^b77.8$ and $K^d19.2$) were highly metastatic (except for the group of mice immunized with $K^b77.8$ and challenged i.f.p. with D122 cells; this group of mice showed moderate metastasis). Mice immunized with the double transfected D122 cells (Kd.b85 and Kd.b95) were non-metastatic in both types of challenge.

Table 14 summarizes the results of the metastatic phenotypes of D122 cells in C3B6/F1 ($H_2^b$, $H_2^k$) immunized mice. Mice were immunized with D122, $K^b77.8$, $K^k4.1$, K-2 and Kk.b72 and subsequently challenged i.f.p. with D122 cells. 30 days after amputation mice were sacrificed and metastatic load was evaluated. Again, the control group, mice immunized with D122 parental cells, was highly metastatic. Similarly, mice immunized with the single transfectants ($K^b77.8$ and $K^k4.1$) were highly metastatic. In contrast, mice immunized with the double transfectants (Kk.b72 and K-2) were nonmetastatic. There was no difference in the growth rates of tumors between the control group and the immunized mice.

The results of the i.v. challenge were slightly different from the results of thereof m.p. challenge. The control group of mice immunized with the parental D122 cells and mice immunized with the single $K^b77.8$ transfectant were highly metastatic after i.v. challenge with D122 cells, but the single transfectant $K^k4.1$ was moderately metastatic (p-values, 0.0055, Table 14), whereas the double transfectants (kk.b72 and K-2) were non-metastatic.

Experiments with (BL×BM1)/F1 mice immunized with $K^b,K^{bm1}$/D122 double transfectants are consistent with the other types of F1 mice.

To summarize the protection experiments in both the F1 mice and in C57BL/6 mice, immunization with the single or double transfectants had no effect on the growth rates of the parental D122 cells. The major benefit of the immunization with the double transfectants both in F1 and C57BL/6 mice was complete abolishment of the metastatic spread of D122 parental cells in mice immunized with either $K^b,K^d$/D122 or $K^b,K^k$/D$_{122}$ cells.

Immunization with the single transfectants succeeded in some cases to reduce the metastatic phenotype but did not abolish it completely.

EXAMPLE 15

In vitro cytotoxicity assays in C57BL/6 mice

The in vivo results indicate that the reduction in metastatic phenotype of the double transfectants is due to the interaction with mature T cells since in T cell deficient nude mice all clones show a highly metastatic phenotype. In addition, immunization by double transfectants of both C57BL/6 and F1 mice affords protection against metastatic spread of D122 parental cells, indicating participation of a tumor-specific memory-dependent immune response. It was therefore tested by in vitro cytotoxicity assays whether the reduction of the metastatic phenotype of D122 cells in immunized mice is correlated with the action of cytotoxic T cells.

C57BL/6 mice were immunized by three intraperitoneal injections of 2×10⁶ cells grown in tissure culture, irradiated at 5000 Rad and treated with 80 µg/ml mitomycin-C for 1 hr, given at 7-day intervals. Spleens were removed 10 days after the third injection and splenocytes were resensitized for 5 days on monolayers of irradiated cells as used for the immunizations. These splenocytes were used as effector cells in cytotoxicity assays.

FIG. 13 and Table 15 summarize the results of anti-$K^b$, $K^d$/D122 CTLs produced in C57BL/6 mice. Table 15 shows:

(1) Mice immunized with the parental D122 cells did not produce measurable levels of anti-tumor CTLs since none of the target cells were lysed.

(2) Mice immunized with the single transfectant $K^b77.8$ produced low levels of CTLs that seem to be $K^b$-restricted anti-tumor CTLs since tumor cells expressing high levels of $K^b$ (Kd.b85, Kd.b95, see Table 16) were lysed more efficiently than expressing low levels of $K^b$ ($K^b77.8$, $K^d19.2$, D122) while other cells used as a control (see below) were not lysed at all.

(3) Mice immunized with the single transfectant $K^d19.2$ produced mainly alloreactive CTLs (anti-H-2$K^d$) that efficiently kill $K^d$-carrying targets. $K^d19.2$ double transfectants or the DBA/2 derived mastocytoma (H-2$^d$)-P815. However, the CTLs also kill to some extent $K^b77.8$ and D122 parental cells.

(4) Mice immunized with the double transfectants produced high levels of CTLs against all specific target cells tested and against P815 but not against EL-4 or YAC cells. The levels of $K^b$-restricted anti-tumor CTLs are high, as judged from the lysis of $K^b77.8$ and D122 cells. For example, CTLs produced against the single transfectant $K^b77.8$ killed 11% of $K^b77.8$ and 10% of D122 cells (at a ratio of 100:1) while CTLs produced against the double transfectant Kd.b85 killed 79% of $K^b77.8$ and 31% of D122 parental cells.

EL-4, YAC and P-815 target cells were used as a control. EL-4 is a T-cell lymphoma line derived from C57BL/6 mice ($H_2^b$ haplotype) that is sensitive to lysis by CTLs that recognize H-2. YAC cells (H-2$^k$ haplotype) are a line that is known to be sensitive to killing by NK cells. P815 mastocytoma is a line derived from DBA/2 mice (H-2$^d$ haplotype) that is known to be sensitive to killing by CTLs that recognize the H-2$^d$ haplotype.

EL-4 target cells were not killed by any CTLs produced against any of the clones described in the invention (Table 15), indicating that the CTL populations did not contain anti-$K^b$ reactivity.

YAC cells were also not killed by the various CTLs (Table 15), indicating that the CTL populations did not contain any NK activity.

The single transfectant $K^d19.2$ and the double transfectants Kd.b85 and Kd.b95 express the H-2$K^d$ gene; as expected C57BL/6 mice (H-2$^b$ haplotype) that were immunized with these clones produced allogeneic CTLs. Table 15 shows that in the CTL populations produced after immunization of C57BL/6 mice with the single transfectant $K^d19.2$ and the double transfectants, anti-$K^d$ reactivity against P-815 cells (H-2$^d$ haplotype) was high.

The anti-$K^b,K^d$/D122 CTLs were found to kill D122 cells more efficiently than CTLs induced by the single transfectants or the parental D122 cells (Table 15 and FIG. 13).

FIG. 13 shows the lytic activity of CTLs elicited by D122, single transfectants and double transfectants at different effector-to-target ratios against D122 target cells. In all effector-to-target ratios, CTLs that were produced against the double transfectants kill more efficiently the parental D122 target cells than CTLs that were produced against the single transfectants.

In vitro cytotoxicity assay with $K^b,K^k$/D122 transfectants

Table 16 and FIG. 14 show in vitro lytic activity of CTLs elicited in C57BL/6 mice by D122, single transfectants ($K^b77.8$ and $K^k4.1$) and double transfectants (Kk,b72 and K-2) against the same clones as target cells. EL-4 ($H-2^b$), YAC (NK sensitive cells) and L-cells ($H-2^k$) were used as controls. Again, mice immunized with the non-transfected D122 cells did not produce measurable levels of CTLs. Mice immunized with the single transfectant $K^b77.8$ produced moderate levels of CTLs that killed double transfectants, the $K^b77.8$ single transfectant and D122 parental cells. surprisingly, also the allogeneic single transfectant $K^k4.1$ that expresses very low $H-2K^b$ levels (Table 2) was killed by anti-$K^b77.8$ CTLs (Table 16). anti-77.8 CTLs also lysed 7% of the EL-4 target cells at effector-to-target ratio of 100:1 indicating that the CTL population contained some anti-$K^b$ reactivity. anti-$K^b77.8$ did not lyse L-cells or YAC cells indicating that the CTL population did not contain anti-$K^k$ reactivity or any NK activity (Table 16).

Anti-$K^k4.1$ CTLs efficiently killed $K^k4.1$ and Kk,b72 target cells at levels of 59% and 56% killing, respectively, at effector-to-target ratios of 100:1 (Table 16); K-2 cells were lysed only at a percentage of 22% at the same effector-to-target ratio. $K^k4.1$ and Kk,b72 target cells express high levels of the $H-2K^k$ gene while K-2 expresses low levels of $H-2K^k$ (Table 2). The anti-$K^k4.1$ CTL population does not contain anti-$H-2^b$ reactivity as observed from the resistance of EL-4 cells to cytotoxic activity (Table 16), but seems to contain high levels of allogeneic CTLs: 60% killing of L-cells at an effector-to-target ratio of 100:1 was observed (Table 16). However, this CTL population also shows a $K^b$-restricted anti-tumor activity: 19% killing of the $K^b77.8$ target cells by anti-$K^k4.1$ CTLs at an effector-to-target ratio of 100:1 and 44% killing of D122 cells was observed. The killing of the YAC cells by allogeneic anti-$H-2K^k4.1$ or Kk,b double transfectants is not due to the NK activity but rather to the fact that the YAC cells that originated in an $H-2^a$ mouse carry the $H-2K^k$ gene. Anti-K-2 CTLs efficiently killed all target cells tested except $K^k4.1$ target cells. This moderate killing (i.e. lower than 30% target cell killing) is probably due to the low expression of the $H-2K^k$ MHC antigen on the cell surface of the double transfectant K-2 (Table 2). Anti-K-2 CTL populations do not contain anti-$K^k$ reactivity (0% killing of the EL-4 target cells, Table 16). The anti-K-2 CTL population shows, however, high anti-$K^k$ activity.

Anti-Kk,b72 CTLs efficiently kill D122, $K^k4.1$ and Kk,b72 target cells (Table 16). Only 26% and 18% of the target cells $K^b77.8$ and K-2, respectively, at an effector-to-target ratio of 100:1 were killed by anti-Kk,b72 CTLs. This moderate killing is due to the low expression of the $H-2K^b$ MHC antigen on the cell surface of the Kk,b72 double transfectant and the high expression of the $H-2K^b$ MHC antigen on the $K^b77.8$ and K-2 target cells (Table 2). Thus, anti-Kk,b72 CTLs contain high levels of $H-2K^k$ restricted T cells and relatively moderate levels of $H-2K^b$ restricted T cells that kill moderately $H-2K^b$ expressing cells.

The anti-Kk,b72 CTL population also contains high levels of anti-$K^k$ activity and does not contain anti-$K^b$ reactivity (Table 16).

The anti-$K^b,K^k$/D122 CTLs were found to efficiently kill the parental D122 target cells. The anti-double transfectant CTLs kill the parental D122 target cells more efficiently than the anti-single transfectants CTLs in all effector-to-target ratios that were tested (Table 16 and FIG. 14).

In vitro cytotoxicity assay with $K^b,K^{bm1}$/D122 transfectants Table 17 and FIG. 15 show the in vitro lytic activity elicited by D122 single transfectants ($K^b77.8$ and $K^{bm1}25.1$) and the double transfectants (Kbm1,b4 and Kbm1,b68) on the same tumor cells as targets. EL-4 cells and YAC cells were used as controls for anti-$K^b$ reactivity and NK reactivity, respectively. Again, mice immunized with the non-transfected D122 cells did not produce specific CTLs. Mice immunized with the single transfectants produced moderate levels of CTLs against the target cells tested. Homologous target cells were lysed more efficiently than heterologous target cells. Mice immunized with the double transfectants produced the highest level of CTLs that efficiently kill specific target cells, but not EL-4 or YAC cells. Only the anti-$K^b77.8$ CTL population contains a low level of anti-$K^b$ reactivity.

FIG. 15 shows the in vitro lytic activity against D122 target cells of CTLs elicited by D122, single transfectants and double transfectants at different effector-to-target ratios. Again, it can be seen that the most efficient killing was effected by CTLs specific for the double transfectants in all effector-to-target ratios.

The main conclusion from the in vitro cytotoxicity assays in C57BL/6 mice are:
(1) Immunization with the parental D122 cells did not induce the production of specific CTLs.
(2) Immunization with the double transfectants induced the production of specific CTLs that efficiently kill D122 derived target cells, usually at much higher levels than CTLs obtained after immunization with the single transfectants.
(3) CTLs derived from mice immunized with the double transfectants efficiently kill the parental D122 target cells, while mice immunized with the single transfectants produced much lower levels of CTLs and were less efficient in killing the parental D122 target cells.

EXAMPLE 16
In vitro cytotoxicity assays in F1 mice
F1 mice were immunized three times as described in Example 17. In vitro cytotoxicity assays were performed 10 days after the third boost.
In vitro cytotoxicity assays with $K^b,K^d$/D122 transfectants in CB6/F1 mice Table 18 shows in vitro lytic activity of CTLs elicited by D122, single transfectants ($K^b77.8$ and $K^d19.2$) and double transfectants (Kd,b85 and Kd,b95) on the same tumor cells. EL-4 cells, YAC cells and P-815 cells were used as controls for anti-$K^b$ reactivity, NK activity, and anti-$K^d$ reactivity, respectively.

Immunization with D122 parental cell did not produce CTLs. Immunization with the single transfectant $K^b77.8$ produced low levels of CTLs. The anti-$K^b77.8$ population showed to a very low extent killing of target cells (D122, $K^d19.2$) expressing low levels of $K^b$ and somewhat higher killing of target cells expressing $K^b$. No killing of heterologous cells EL-4, YAC or P-815 was observed. Immunization with $K^d19.2$ produced high levels of CTLs against $K^d19.2$, Kd,b85 and Kd,b95 at an effector-to-target ratio of 100:1, but the levels of CTLs decreased markedly at an effector-to-target ratio of 50:1. Immunization with $K^d19.2$ produced low levels of CTLs against the parental D122 cells and moderate levels of CTLs against $K^b77.8$ target cells. Since both H-2K alleles are compatible with the immunized host (no alloreaction), these results indicate that TAA can be effectively presented by $H-2K^d$ molecules.

Immunization with both double transfectants produced CTLs that compared to immunization with the single transfectants killed the target cells more efficiently at both effector-to-target ratios of 100:1 and 50:1. All the CTL populations tested in this assay do not contain anti-$K^b$ and anti-$K^d$ reactivity or NK activity.

FIG. 16 shows the in vitro lytic activity curves of CTLs elicited by D122, single transfectants and double transfectants against the non-transfected D122 target cells at different effector-to-target ratios. It can be seen that immunization with the double transfectants produced CTLs that efficiently killed the parental D122 target cells, while mice immunized with the single transfectants produced much lower levels of CTLs.

In vitro cytotoxicity assays with $K^b, K^k$ transfectants in C3B6/F1 mice

Table 19 shows the in vitro lytic activity produced by D122, single transfectants ($K^b77.8$ and $K^k4.1$) and double transfectants (K-2 and Kk.b72). The data show percent specific lysis obtained with effector-to-target ratios of 100:1 and 50:1. EL-4 cells, YAC cells and L-cells were used as controls. Again, immunization with the parental D122 cells did not produce CTLs. Immunization with the single transfectant $K^b77.8$ produced CTLs that lysed with low efficiency D122 and $K^k4.1$ target cells, with high efficiency $K^b77.8$ and K-2 target cells (both target cells express high levels of H-2$K^b$ class I MHC antigen) and with moderate efficiency Kk.b72 cells.

Immunization with the single transfectant $K^k4.1$ produced CTLs that efficiently killed $K^k4.1$ and Kk.b72 target cells (high $K^k$ expresser) and were less efficient against K-2 target cells (low $K^k$ expresser). $K^b77.8$ cells were poorly lysed by these CTLs, but high reactivity against D122 cells was observed. Again, immunization with the double transfectants generally produced the highest level of CTLs that efficiently killed the various target cells. There was no anti-$K^b$ or anti-$K^k$ reactivity or NK activity among the CTL populations.

FIG. 17 shows the in vitro lytic activity of the CTLs produced by D122, single transfectants and double transfectants against the parental D122 target cells. Again, it can be seen that mice immunized with the double transfectants produced CTLs that efficiently killed the parental D122 target cells, while mice immunized with the single transfectants produced much lower levels of CTLs in all effector-to-target ratios tested.

In vitro cytotoxicity assays with $K^b, K^{bm1}$/D122 transfectants in (BL×BMb 11)F1 mice Table 20 shows the in vitro lytic activity of CTLs produced by D122, single transfectants ($K^b77.8$ and $K^{bm1}25.1$) and a double transfectant (Kbm1.b68). The data show percent specific lysis obtained with effector-to-target ratios of 100:1 and 50:1. Immunization with the parental non-transfected D122 cells did not lead to the production of specific CTLs. Immunization with the single transfectants $K^b77.8$ and $K^{bm1}25.1$ produced generally low levels of specific CTLs. Again, mice immunized with the double transfectant Kbm1.b68 led to the production of high levels of CTLs compared to the other immunization schedules (single transfectants or parental D122). All the CTL populations do not contain anti-$K^b$ reactivity or NK activity. FIG. 18 shows the in vitro lytic activity elicited by D122, single transfectants and the double transfectant Kbm1.b68 on D122 target cells at different effector-to-target ratios. It can be seen that immunization with the double transfectant Kbm1.b68 was most efficient. The most efficient killing of the parental D122 target cells was by anti-Kbm1.b68 CTLs in all effector-to-target ratios tested. The conclusions from the in vitro cytotoxicity assays in F1 mice are:

(1) Immunization with the parental D122 cells did not induce the production of specific CTLs.
(2) Immunization with the double transfectants was the most efficient and led to the production of CTLs with high killing activity against all specific target cells tested.
(3) The most efficient killing of the parental non-transfected D122 target cells was effected by anti-double transfectant CTLs.

EXAMPLE 17

The long-term memory of the immune response Mice that did not grow the primary tumor after 120–150 days were boosted by an i.p. injection of $2 \times 10^6$ irradiated and mitomycin-C treated tumor cells as used in the first injection. Ten days after the boost, mice were challenged by an i.f.p. injection with parental D122 cells. The growth of the D122 parental cells in the mice is summarized in Table 21. Neither the C57BL/6 mice nor the F1 mice grew D122 tumors, while in the control group (naive mice injected with D122 cells) the parental D122 cells grew in all of the mice.

It can be concluded that the rejection of the primary tumor in the first injection created memory cells that after the boost produced CTLs that efficiently killed the parental D122 cells and prevented the growth of the tumor.

EXAMPLE 18

Prevention of metastasis formation of mice already carrying a parental tumor

Figure 19:
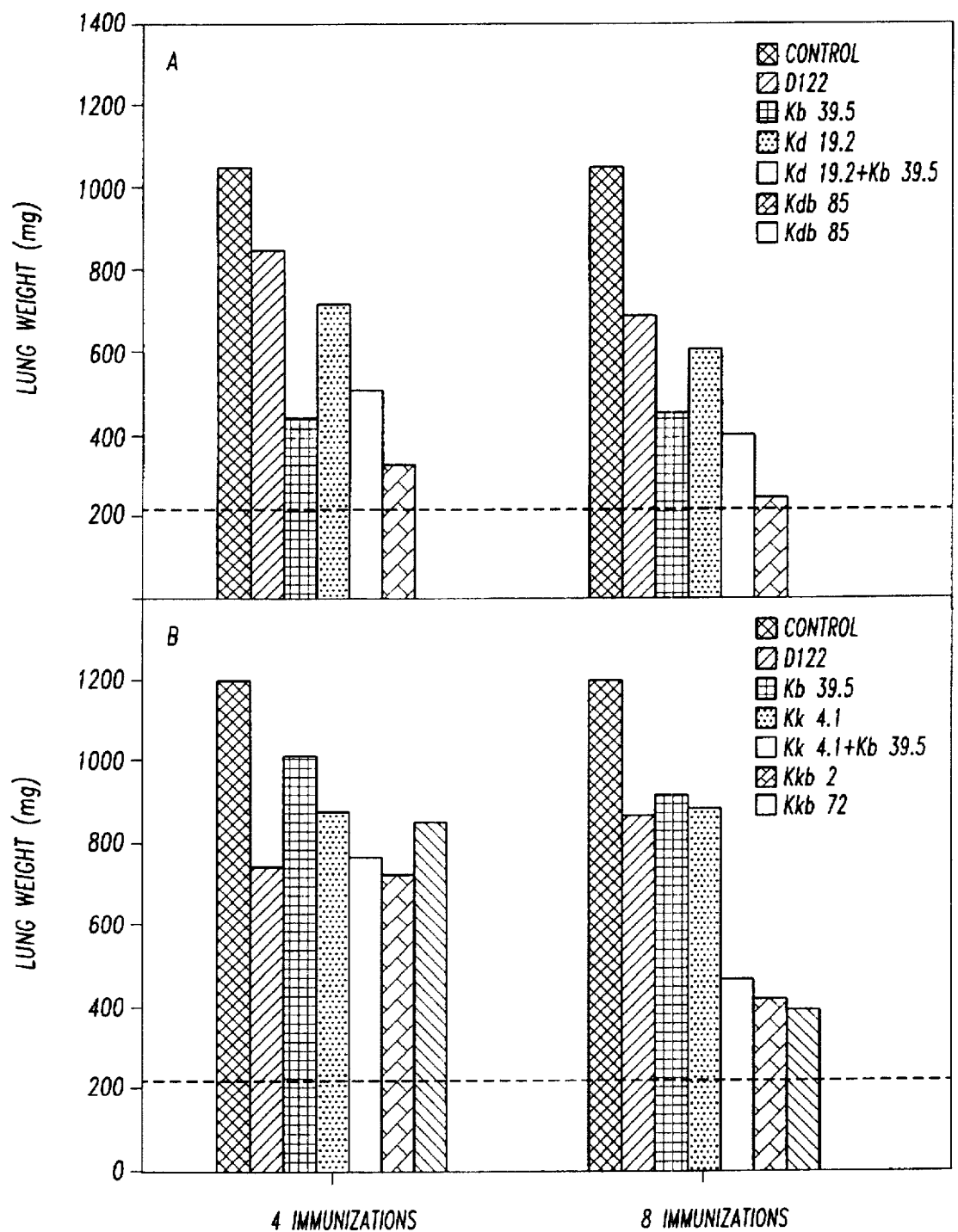

To study whether the anti-metastatic immunity can act in preventing metastasis formation in animals already carrying a parental tumor, groups of mice were inoculated i.f.p. with $2 \times 10^5$ D122 cells. Starting at day 8 after inoculation, when palpable local tumors could be detected, groups of mice were immunized by four or eight i.p. weekly injections of irradiated and mitomycin-C treated cells. FIG. 19 shows that in CB6/F1, metastases of D122 cells did not develop in animals injected eight times with Kdb85 (p value=0.0001). only a few metastases developed in animals immunized four times with Kdb85 cells (p value=0.0001). Immunization with the single transfectant Kdb39.5 had only a partial effect (four immunizations p value=0.0198, eight immunizations, p value=0.0001). The single transfectant Kd19.2 (low $K^b$ expressor) showed an even lower therapeutic effect (for 4 and 8 immunizations, p values were 0.0573 and 0.0752, respectively). Interestingly, a mixture of Kdb39.5 and Kd19.2 cells was not as effective as the double transfectant. A comparison of the p values for the results with the double transfectant and the mixture of single transfectants yielded statistically significant differences following eight immunizations (eight immunizations p value=0.0356; four immunizations p value=0.0539). A slightly different picture was observed in C3B6/F1 mice (FIG. 19). Groups of mice immunized four times with any of the clones showed no statistically significant reduction in metastatic loads, while 8 immunizations with the double transfectants reduced the metastatic load (p values were 0.0544 and 0.04 for Kkb2 and Kkb72, respectively). Prevention of metastasis formation was also observed in mice immunized with the mixture of the single transfectants Kb39.5 and Kk4.1. Although the average lung weights of this group and the group immunized with the double transfectants were similar, the former group showed heterogeneity in lung weights among individual mice. Statistical evaluation showed a p value of 0.06 relative to the control group. Single transfectants had no significant effect on development of metastases. In conclusion, the immunogenic effects evoked by double transfectants effectively prevented or reduced the formation of metastases by an established tumor.

TABLE 1

Expression of MHC class I in $K^d$, $K^b$ D122 transfectants

| Clone | Transfected gene | $K^d$ | $K^b$ ng/5 × 10⁵cells | $D^b$ |
|---|---|---|---|---|
| D122 | — | 0 | 0.38 | 7.20 |
| $K^d$,19.2 | $K^d$ | 38.00 | 0.45 | 10.00 |
| $K^b$77.8 | $K^b$ | 0 | 1.00 | 6.70 |
| $K^b$39.5 | $K^b$ | 0 | 3.00 | 6.30 |
| $K^{d,b}$24 | $K^d K^b$ | 24.00 | 4.00 | 7.20 |
| $K^{d,b}$70 | $K^d K^b$ | 19.00 | 2.50 | 6.00 |
| $K^{d,b}$75 | $K^d K^b$ | 18.00 | 6.70 | 6.40 |
| $K^{d,b}$80 | $K^d K^b$ | 23.00 | 3.30 | 5.50 |
| $K^{d,b}$85 | $K^d K^b$ | 27.00 | 6.20 | 7.70 |
| $K^{d,b}$95 | $K^d K^b$ | 57.00 | 5.50 | 6.30 |
| $K^{d,b}$5 | $K^d K^b$ | 10.00 | 3.40 | 7.00 |

Direct RIA, were performed with monoclonal antibodies K-10-18-9 ($\alpha K^d$), K-9-178 ($\alpha K^b$) and 28-14-8 ($\alpha D^b$) as described in Example 3. The results are presented by ng antibody bound/5 × 10⁵cells.

TABLE 2

Expression of MHC class I in $K^k$,$K^b$ D122 transfectants

| Clone | Transfected gene | $K^k$ | Kb ng/5 × 10⁵cells | $D^b$ |
|---|---|---|---|---|
| D122 | — | 0 | 0.38 | 7.20 |
| $K^k$4.1 | $K^k$ | 30.00 | 0.12 | 5.90 |
| $K^b$77.8 | $K^b$ | 0 | 1.00 | 6.70 |
| $K^b$39.5 | $K^b$ | 0 | 3.00 | 6.30 |
| K-2 | $K^k,K^b$ | 0.35 | 1.80 | 6.00 |
| $K^{k,b}$28 | $K^k,K^b$ | 27.00 | 1.60 | 5.00 |
| $K^{k,b}$72 | $K^k,K^b$ | 20.00 | 1.00 | 5.10 |
| $K^{k,b}$74 | $K^k,K^b$ | 30.00 | 1.50 | 3.20 |
| $K^{k,b}$83 | $K^k,K^b$ | 16.00 | 0.60 | 4.70 |
| $K^{k,b}$13 | $K^k,K^b$ | 0.40 | 1.00 | 6.70 |

Direct RIA* were performed with monoclonal antibodies 16-3-1 ($\alpha K^k$), 20-8-4 ($\alpha K^b$) and 28-14-8 ($\alpha D^b$) as described in Example 3. The results are presented by ng antibody bound/5 × 10⁵ cells.

TABLE 3

Expression of MHC class I in $K^{bm1}$, $K^b$D122 transfectants

| Clone | Transfected gene | $K^{bm1}$ | Kb ng/5 × 10⁵cells | $D^b$ |
|---|---|---|---|---|
| D122 | — | 0 | 0.38 | 7.20 |
| $K^{bm1}$25.1 | $K^{bm1}$ | 5.70 | 0.50 | 6.10 |
| $K^b$77.8 | $K^b$ | 0 | 1.00 | 6.70 |
| $K^b$39.5 | $K^b$ | 0 | 3.00 | 6.30 |
| $K^{bm1,b}$4 | $K^{bm1},K^b$ | 3.40 | 1.10 | 5.20 |
| $K^{bm1,b}$7.1 | $K^{bm1}K^b$ | 6.30 | 1.20 | 6.00 |
| $K^{bm1,b}$12 | $K^{bm1}K^b$ | 4.10 | 1.30 | 6.70 |
| $K^{bm1,b}$68 | $K^{bm1}K^b$ | 40.00 | 1.86 | 6.00 |
| $K^{bm1,b}$14 | $K^{bm1}K^b$ | 1.00 | 1.25 | 6.80 |
| $K^{bm1,b}$19 | $K^{bm1}K^b$ | 1.40 | 0.95 | 6.90 |

Direct RIA* were performed with monoclonal antibodies K9-178 ($\alpha K^b$ not cross reactive with $K^{bm1}$) 20-8-4 binds to both $K^b$ and $K^{bm1}$) and 28-14-8 ($\alpha D^b$) as described in Example 3.
$K^{bm1}$ levels were calculated by the difference between binding of antibodies 20-8-4 and K9-178. The results are presented by ng antibody bound/5 × 10⁵ cells.

TABLE 4

| | Clone | Weight X ± S.D | Med | Growth |
|---|---|---|---|---|
| | Spontaneous metastasis (i.f.p) | | | |
| Parental | D122 | 1246 ± 273 | 1290 | 8/8 |
| Single | $K^b$ 77.8 | 201 ± 17 | 203 | 8/8 |
| transfectants | $K^d$ 19.2 | 243 ± 25 | 245 | 8/8 |
| Double | Kd,b 24 | 251 ± 89 | 268 | 4/8 |
| transfectants | Kd,b 70 | 207 ± 16 | 207 | 3/8 |
| | Kd,b 75 | 264 ± 44 | 261 | 4/8 |
| | Kd,b 80 | 207 ± 11 | 213 | 4/8 |
| | Kd,b 85 | primary tumor did not grow | | 0/8 |
| | Kd,b 95 | primary tumor did not grow | | 0/8 |
| | Kd,b 5 | 253 ± 24 | 249 | 8/8 |
| | Experimental metastasis | | | |
| Parental | D122 | 1230 ± 190 | 1300 | |
| Single | $K^b$ 77.8 | 249 ± 30 | 260 | |
| transfectants | $K^d$ 19.2 | 243 ± 17 | 242 | |
| Double | Kd,b 24 | 258 ± 16 | 259 | |
| transfectants | Kd,b 70 | 230 ± 48 | 215 | |
| | Kd,b 75 | 224 ± 70 | 220 | |
| | Kd,b 80 | 256 ± 17 | 249 | |
| | Kd,b 85 | 245 ± 22 | 230 | |
| | Kd,b 95 | 223 ± 13 | 212 | |
| | Kd,b 5 | 254 ± 38 | 255 | |

Metastatic phenotypes of D122, single transfectants, and $K^b,K^d$/D122 double transfectants in C57BL/6 mice. The table summarizes the results of i.f.p. and i.v. experiments. 8 mice were injected per group.

TABLE 5

| | Clone | Weight mg X ± S.D | Med | Growth |
|---|---|---|---|---|
| | Spontaneous metastasis (i.f.p.) | | | |
| Parental | D122 | 1246 ± 73 | 1290 | 8/8 |
| Single | $K^b$ 77.8 | 201 ± 17 | 203 | 8/8 |
| transfectants | $K^k$ 4.1 | 277 ± 27 | 263 | 8/8 |
| Double | Kk,b 28 | 330 ± 134 | 310 | 3/8 |
| transfectants | Kk,b 72 | primary tumor did not grow | | 0/8 |
| | Kk,b 74 | primary tumor did not grow | | 0/8 |
| | Kk,b 83 | primary tumor did not grow | | 0/8 |
| | K-2 | primary tumor did not grow | | 0/8 |
| | Experimental metastasis | | | |
| Parental | D122 | 1197 ± 49 | 1300 | |
| Single | $K^b$ 77.8 | 249 ± 30 | 260 | |
| transfectants | $K^k$ 4.1 | 220 ± 29 | 238 | |
| Double | Kk,b 28 | not done | not done | |
| transfectants | Kk,b 72 | 231 ± 27 | 247 | |
| | Kk,b 74 | not done | not done | |
| | Kk,b 83 | not done | not done | |
| | K-2 | 247 ± 29 | 246 | |

Metastatic phenotypes of D122, single transfectants, and $K^b,K^k$/D122 double transfectants in C57BL/6 mice. The table summarizes the results of i.f.p. and i.v experiments. 8 mice were injected per group.

TABLE 6

| | Clone | Weight mg X ± S.D | Med | Growth |
|---|---|---|---|---|
| | Spontaneous metastasis (i.f.p.) | | | |
| Parental | D122 | 929 ± 23 | 884 | 8/8 |
| Single | $K^b$ 77.8 | 201 ± 17 | 203 | 8/8 |
| transfectants | $K^{bm1}$ 25.1 | 199 ± 16 | 193 | 8/8 |
| Double | Kbm1,b 68 | 232 ± 36 | 230 | 4/8 |
| transfectants | Kbm1,b 7.1 | 207 ± 16 | 200 | 4/8 |
| | Kbm1,b 12 | 253 ± 38 | 255 | 8/8 |
| | Kbm1,b 4 | 238 ± 18 | 232 | 8/8 |

TABLE 6-continued

| | Clone | Weight mg X ± S.D | Med | Growth |
|---|---|---|---|---|
| | | Experimental metastasis | | |
| Parental | D122 | 970 ± 295 | 943 | |
| Single | $K^b$ 77.8 | 249 ± 30 | 260 | |
| transfectants | $K^{bm1}$ 25.1 | 206 ± 19 | 260 | |
| Double | Kbm1,b 68 | not done | not done | |
| transfectants | Kbm1,b 7.1 | not done | not done | |
| | Kbm1,b 12 | 165 ± 30 | 175 | |
| | Kbm1,b 4 | 183 ± 28 | 189 | |

Metastatic phenotypes of D122, single transfectants and $K^b,K^{bm1}$/D122 double transfectants in C57BL/6 mice. The table summarizes the results of i.f.p. and i.v. experiments. 8 mice were injected per group.

TABLE 7

| | Clone | Weight (mg) X ± S.D | Med | Growth |
|---|---|---|---|---|
| | | Spontaneous metastasis (i.f.p) | | |
| Parental | D122 | 913 ± 172 | 850 | 8/8 |
| Single | $K^b$ 77.8 | 943 ± 178 | 810 | 8/8 |
| transfectants | $K^d$ 19.2 | 1148 ± 186 | 1200 | 8/8 |
| Double | Kd,b 24 | primary tumor did not grow | | 0/8 |
| transfectants | Kd,b 70 | 249 ± 43 | 249 | 5/8 |
| | Kd,b 75 | primary tumor did not grow | | 0/8 |
| | Kd,b 80 | 224 ± 30 | 244 | 6/8 |
| | Kd,b 85 | 214 ± 26 | 214 | 4/8 |
| | Kd,b 95 | 250 ± 17 | 250 | 3/8 |
| | | Experimental metastasis | | |
| Parental | D122 | 947 ± 205 | 917 | |
| Single | $K^b$ 77.8 | 960 ± 200 | 950 | |
| transfectants | $K^d$ 19.2 | 816 ± 272 | 763 | |
| Double | Kd,b 24 | 187 ± 34 | 183 | |
| transfectants | Kd,b 70 | 236 ± 15 | 243 | |
| | Kd,b 75 | 231 ± 56 | 237 | |
| | Kd,b 80 | 234 ± 48 | 239 | |
| | Kd,b 85 | 221 ± 64 | 202 | |
| | Kd,b 95 | 189 ± 18 | 185 | |

Metastatic phenotypes of D122, single transfectants, and $K^b,K^d$/D122 double transfectants in C36/F1 mice. The table summarizes the results of i.f.p. and i.v. experiments. 8 mice were injected per group.

TABLE 8

| | Clone | Weight (mg) X ± S.D | Med | Growth |
|---|---|---|---|---|
| | | Spontaneous metastasis (i.f.p.) | | |
| Parental | D122 | 1030 ± 66 | 850 | 8/8 |
| Single | $K^b$ 77.8 | 940 ± 200 | 953 | 8/8 |
| transfectants | $K^k$ 4.1 | 1164 ± 427 | 1060 | 8/8 |
| Double | Kk,b 72 | primary tumor did not grow | | 0/8 |
| transfectants | Kk,b 74 | 311 ± 76 | 280 | 3/8 |
| | Kk,b 83 | primary tumor did not grew | | 0/8 |
| | K-2 | primary tumor did not grow | | 0/8 |
| | | Experimental metastasis | | |
| Parental | D122 | 1197 ± 349 | 1300 | |
| Single | $K^b$ 77.8 | 1200 ± 400 | 1090 | |
| transfectants | $K^k$ 4.1 | 1096 ± 348 | 1173 | |
| Double | Kk,b 72 | 231 ± 27 | 247 | |
| transfectants | Kk,b 74 | 328 ± 64 | 317 | |
| | Kk,b 83 | not done | not done | |
| | K-2 | 261 ± 34 | 258 | |

Metastatic phenotypes of D122, single transfectants, and $K^b,K^k$/D122 double transfectants in C3B6/F1 mice. The table summarizes the results of i.f.p. and i.v. experiments. 8 mice were injected per group.

TABLE 9

| | Clone | Weight (mg) X ± S.D | Med | Growth |
|---|---|---|---|---|
| | | Spontaneous metastasis (i.f.p.) | | |
| Parental | D122 | 1053 ± 323 | 967 | 8/8 |
| Single | $K^b$ 77.8 | 841 ± 148 | 825 | 8/8 |
| transfectants | $K^{bm1}$ 25.1 | 750 ± 106 | 744 | 8/8 |
| Double | Kbm1,b 68 | 249 ± 35 | 232 | 4/8 |
| transfectants | Kbm1,b 7.1 | 243 ± 29 | 235 | 8/8 |
| | Kbm1,b 12 | 228 ± 23 | 255 | 8/8 |
| | Kbm1,b 4 | 255 ± 25 | 232 | 8/8 |

Metastatic phenotypes of D122, single transfectants, and $K^b,K^{bm1}$/D122 double transfectants in (BLXBM1)F1 mice. The table summarizes the results of i.f.p. experiments. 8 mice were injected per group.

TABLE 10

| | Clone | Weight mg X ± S.D | Med | Growth |
|---|---|---|---|---|
| | | Spontaneous metastasis (i.f.p.) | | |
| Parental | D122 | 995 ± 168 | 933 | 8/8 |
| Single | $K^b$ 77.8 | 950 ± 228 | 850 | 8/8 |
| transfectants | $K^d$ 19.2 | 810 ± 163 | 760 | 8/8 |
| | $K^{bm1}$ 25.1 | 1076 ± 197 | 987 | 8/8 |
| | $K^k$ 4.1 | 892 ± 270 | 730 | 8/8 |
| Double | Kd,b 85 | 948 ± 134 | 948 | 8/8 |
| transfectants | Kd,b 95 | 825 ± 116 | 760 | 8/8 |
| | Kk,b 72 | 1093 ± 253 | 1017 | 8/8 |
| | K-2 | 922 ± 141 | 949 | 8/8 |
| | Kbm1,b 4 | 874 ± 225 | 874 | 8/8 |
| | Kbm1,b 68 | 1285 ± 185 | 1285 | 8/8 |

Metastatic phenotypes of D122, single transfectants, and $K^b,K^k$/D122 double transfectants in nude mice. The table summarizes the results of i.f.p. experiments. 8 mice were injected per group.

TABLE 11

| Immunization | Challenge | Weight (mg) X ± S.D | Med | P |
|---|---|---|---|---|
| | | Spontaneous metastasis (i.f.p) | | |
| Control | D122 | 1034 ± 311 | 1065 | — |
| D122 | D122 | 942 ± 239 | 1034 | 0.7756 |
| $K^b$ 77.8 | D122 | 518 ± 166 | 526 | 0.1848 |
| $K^d$ 19.2 | D122 | 733 ± 308 | 650 | 0.3652 |
| Kd,b 85 | D122 | 210 ± 14 | 218 | 0.0001 |
| Kd,b 95 | D122 | 203 ± 21 | 206 | 0.0001 |
| | | Experimental metastasis | | |
| Control | D122 | 780 ± 265 | 682 | — |
| D122 | D122 | 854 ± 167 | 867 | 0.5121 |
| $K^b$ 77.8 | D122 | 533 ± 79 | 486 | 0.1343 |
| $K^d$ 19.2 | D122 | 831 ± 75 | 857 | 0.9070 |
| Kd,b 85 | D122 | 219 ± 23 | 206 | 0.0001 |
| Kd,b 95 | D122 | 228 ± 41 | 211 | 0.0001 |

Metastatic growth of D122 cells in C57BL/6 mice immunized with D122, single transfectants ($K^b$ 77.8 and $K^d$ 19.2) and double transfectants (Kd,b 85 and Kd,b 95). Naive (as a control) and immunized mice were injected i.f.p. and i.v. as described in Example 13. Mice were immunized three times at 7-day intervals by i.p injection of $2 \times 10^6$ irradiated and mitomycin C treated cells p values were calculated by unpaired two tail t-test. They described the probability that the mean value of the control group and the mean value of the immunized group are not different. Biologically, p < 0.05 indicates significant difference between the two mean values.

TABLE 12

| Immunization | Challenge | Weight mg X ± S.D | Med | P |
|---|---|---|---|---|
| Spontaneous metastasis | | | | |
| Control | D122 | 1034 ± 311 | 1065 | — |
| D122 | D122 | 942 ± 239 | 1034 | 0.7756 |
| $K^b$ 77.8 | D122 | 518 ± 166 | 526 | 0.1848 |
| $K^k$ 4.1 | D122 | 757 ± 348 | 625 | 0.3969 |
| K-2 | D122 | 316 ± 76 | 287 | 0.0020 |
| Kk,b 72 | D122 | 169 ± 27 | 180 | 0.0001 |
| Experimental metastasis | | | | |
| Control | D122 | 780 ± 265 | 682 | — |
| D122 | D122 | 854 ± 167 | 867 | 0.5121 |
| $K^b$ 77.8 | D122 | 533 ± 79 | 486 | 0.1343 |
| $K^k$ 4.1 | D122 | 449 ± 55 | 480 | 0.0470 |
| K-2 | D122 | 222 ± 20 | 235 | 0.001 |
| Kk,b 72 | D122 | 242 ± 26 | 238 | 0.0001 |

Metastatic growth of D122 cells in C57BL/6 mice immunized with D122, single transfectants ($K^b$ 77.8 and $K^k$ 4.1) and double transfectants (Kk,b 72 and K-2). Naive (as a control) and immunized mice were injected i.f.p. and i.v. as described in Example 13. Mice were immunized three times at 7-day intervals by i.p injection of 2 × 10⁶ irradiated and mitomycin C treated cells (see Methods). p values were calculated by unpaired two tail t-test. They describe the probability that the mean value of the control group and the mean value of the immunized group are not different. Biologically, p < 0.05 indicates significant difference between the two mean values.

TABLE 13

| Immunization | Challenge | Weight mg X ± S.D | Med | P |
|---|---|---|---|---|
| Spontaneous metastasis (i.f.p) | | | | |
| Control | D122 | 821 ± 251 | 891 | — |
| D122 | D122 | 867 ± 263 | 860 | 0.7742 |
| $K^b$ 77.8 | D122 | 566 ± 96 | 584 | 0.0378 |
| $K^d$ 19.2 | D122 | 821 ± 259 | 780 | 0.9930 |
| Kd,b 85 | D122 | 294 ± 42 | 285 | 0.0005 |
| Kd,b 95 | D122 | 275 ± 76 | 285 | 0.0001 |
| Experimental metastasis (i.v) | | | | |
| Control | D122 | 1333 ± 251 | 1436 | — |
| D122 | D122 | 970 ± 244 | 987 | 0.0776 |
| $K^b$ 77.8 | D122 | 1268 ± 240 | 1419 | 0.6698 |
| $K^d$ 19.2 | D122 | 1328 ± 178 | 1337 | 0.9727 |
| Kd,b 85 | D122 | 305 ± 104 | 280 | 0.0001 |
| Kd,b 95 | D122 | 330 ± 71 | 332 | 0.0001 |

Metastatic growth of D122 cells in B6D2/F1 (H-2ᵇ, H-2ᵈ) mice immunized with D122, single transfectants ($K^b$ 77.8 and $K^d$ 19.2) and double transfectants (Kd,b 85 and Kd,b 95). Naive (as a control) and immunized mice were injected i.f.p and i.v. as described in Example 14. Mice were immunized three times at 7-day intervals by i.p. injection of 2 × 10⁶ irradiated and mitomycin C treated cells. p values were calculated by unpaired t-test. They describe the probability that the mean value of the control group and the mean value of the immunized group are not different.
p < 0.05 indicates significant difference between the two mean values.

TABLE 14

| Immunization | Challenge | Weight mg X ± S.D | Med | p |
|---|---|---|---|---|
| Spontaneous metastasis | | | | |
| Control | D122 | 862 ± 324 | 831 | — |
| D122 | D122 | 994 ± 435 | 876 | 0.7559 |
| $K^b$ 77.8 | D122 | 1147 ± 325 | 1298 | 0.3396 |
| $K^k$ 4.1 | D122 | 962 ± 198 | 956 | 0.5396 |
| K-2 | D122 | 283 ± 47 | 299 | 0.0075 |
| Kk, b 72 | D122 | 285 ± 30 | 286 | 0.0074 |
| Experimental metastasis | | | | |
| Control | D122 | 853 ± 245 | 730 | |
| D122 | D122 | 711 ± 102 | 654 | 0.2865 |
| $K^b$ 77.8 | D122 | 721 ± 48 | 679 | 0.3058 |
| $K^k$ 4.1 | D122 | 433 ± 37 | 480 | 0.0055 |
| K-2 | D122 | 187 ± 26 | 190 | 0.0006 |
| Kk,b 72 | D122 | 188 ± 28 | 238 | 0.0006 |

Metastatic growth of D122 cells in C3B6/F1 mice immunized with D122, single transfectants ($K^b$ 77.8 and $K^k$ 4.1) and double transfectants (Kk,b 72 and K-2). Naive (as a control) and immunized mice were injected i.f.p. and i.v. as described in Example 14. Mice were immunized three times at 7-day intervals by i.p. injection of 2 × 10⁶ irradiated and mitomycin C treated cells. p values were calculated by unpaired two tail t-test. They describe the probability that the mean value of the control group and the mean value of the immunized group are not different.
Biologically, p < 0.05 indicates significant difference between the two mean values.

TABLE 15

| immun iztion | Eff/Tar ratio | Target cells (% specific lysis) | | | | | | | |
|---|---|---|---|---|---|---|---|---|---|
| | | D122 | 77.8 | 19.2 | 85 | 95 | EL-4 | YAC | P815 |
| D122 | 100:1 | 0 | 0 | 0 | 0 | 0 | 0 | 0 | 0 |
| | 50:1 | 0 | 0 | 0 | 0 | 0 | 0 | 0 | 0 |
| $K^b$77.8 | 100:1 | 10 | 11 | 9 | 14 | 20 | 0 | 0 | 0 |
| | 50:1 | 4 | 11 | 7 | 3 | 3 | 0 | 0 | 0 |
| $K^d$19.2 | 100:1 | 14 | 14 | 46 | 32 | 22 | 0 | 0 | 27 |
| | 50:1 | 11 | 6 | 41 | 18 | 17 | 0 | 0 | 9 |
| Kdb85 | 100:1 | 31 | 79 | 59 | 63 | 45 | 0 | 0 | 32 |
| | 50:1 | 16 | 20 | 55 | 36 | 22 | 0 | 0 | 20 |
| Kdb95 | 100:1 | 36 | 22 | 79 | 30 | 56 | 0 | 0 | 35 |
| | 50:1 | 29 | 16 | 69 | 23 | 52 | 0 | 0 | 2 |

In vitro lytic activity of CTLs elicited by D122. Single transfectants ($K^b$ 77.8 and $K^d$ 19.2) and double transfectants (Kd,b 85 and Kd,b 95). C57BL/6 mice were immunized three times at 7-day intervals by i.p. injection of 2 × 10⁶ irradiated and mitomycin C treated cells. 10 days later, spleen cells were restimulated in vitro with the tumor cells from the same source, irradiated and mitomycin C treated as before, for 5 days; see Example 5. Data show percent specific lysis obtained with effector-to-target ratios of 100:1 and 50:1. Target cells labeled with 35s methionine were reacted in a 16 hr assay with effector cells.
The percentages were under under 5% of the mean values of the triplicates. $K^{bm1}$ 25.1 is also named DKM 25.1.

TABLE 16

| immun iztion | Eff/Tar ratio | Target cells (% specific lysis) | | | | | | | |
|---|---|---|---|---|---|---|---|---|---|
| | | D122 | 77.8 | 4.1 | K-2 | 72 | EL-4 | YAC | L-cells |
| D122 | 100:1 | 0 | 4 | 0 | 0 | 0 | 0 | 0 | 0 |
| | 50:1 | 0 | 2 | 0 | 0 | 0 | 0 | 0 | 0 |
| $K^b$77.8 | 100:1 | 28 | 20 | 34 | 31 | 31 | 7 | 0 | 0 |
| | 50:1 | 23 | 16 | 20 | 29 | 24 | 7 | 0 | 0 |
| $K^k$4.1 | 100:1 | 44 | 19 | 59 | 22 | 56 | 4 | 14 | 60 |
| | 50:1 | 27 | 15 | 57 | 9 | 41 | 1 | 8 | 49 |
| K-2 | 100:1 | 55 | 34 | 30 | 71 | 60 | 0 | 21 | 76 |
| | 50:1 | 52 | 26 | 26 | 61 | 52 | 0 | 13 | 58 |
| Kkb72 | 100:1 | 56 | 26 | 65 | 18 | 60 | 0 | 17 | 63 |
| | 50:1 | 54 | 12 | 63 | 16 | 60 | 0 | 14 | 55 |

In vitor lytic activity of CTLs elicited by D122, Single transfectants ($K^b$ 77.8 and $K^k$ 4.1) and double transfectants (K-2 and Kk,b 72).

TABLE 16-continued

| immuniztion | Eff/Tar ratio | Target cells (% specific lysis) | | | | | | | |
|---|---|---|---|---|---|---|---|---|---|
| | | D122 | 77.8 | 4.1 | K-2 | 72 | EL-4 | YAC | L-cells |

C57BL/6 mice were immunized three times at 7-day intervals by i.p. injection of $2 \times 10^6$ irradiated and mitomycin C treated cells. 10 days later, spleen cells were restimulated in vitro with the same tumor cells from the same source, irradiated and mitomycin C treated as before, for 5 days; see Example 5. Data show percent specific lysis obtained with effector-to-target ratios of 100:1 and 50:1. Target cells labeled with $^{35}S$ methionine were reacted in a 16 hr assay with effector cells. The cytolytic activity on EL-4, YAC and L-cells (target cells) was determined after 5 hrs. Error percentages were under 5% of the mean values of the triplicates.

TABLE 17

| Immuniztion | Eff/Tar ratio | Target cells (% specific lysis) | | | | | | |
|---|---|---|---|---|---|---|---|---|
| | | D122 | 77.8 | 25.1 | 4 | 68 | EL-4 | YAC |
| D122 | 100:1 | 0 | 4 | 0 | 0 | 0 | 0 | 0 |
| | 50:1 | 0 | 2 | 0 | 0 | 0 | 0 | 0 |
| $K^b$77.8 | 100:1 | 28 | 20 | 10 | 9 | 14 | 7 | 0 |
| | 50:1 | 23 | 16 | 8 | 9 | 5 | 7 | 0 |
| DKM 25.1 | 100:1 | 15 | 18 | 27 | 10 | 11 | 0 | 0 |
| | 50:1 | 13 | 13 | 10 | 5 | 8 | 0 | 0 |
| Kbm1,b4 | 100:1 | 50 | 54 | 36 | 38 | 32 | 0 | 0 |
| | 50:1 | 47 | 41 | 36 | 30 | 29 | 0 | 0 |
| Kbm1,b68 | 100:1 | 62 | 23 | 27 | 16 | 22 | 0 | 0 |
| | 50:1 | 53 | 23 | 26 | 12 | 20 | 0 | 0 |

In vitro lytic activity of CTLs elicited by D122 Single transfectants ($K^b$ 77.8 and DKM 25.1) and double transfectants (kbm1,b4 and Kbm1,b 68). C57B/6 mice were immunized three times at 7-day intervals by i.p injection of $2 \times 10^6$ irradiated and mitomycin C treated cells. 10 days later, spleen cells were restimulated in vitro with the tumor cells from the same source, irradiated and mitomycin C treated as before, for 5 days, see Example 5. Data show percent specific lysis obtained with effector-to-target ratios of 100:1 and 50:1. Target cells labeled with $^{35}S$ methionine were reacted in a 16 hr assay with effector cells. The percentages were under 5% of the mean values of the triplicates. $K^{bm1}$ 25.1 is also named DKM 25.1.

TABLE 18

| Immuniztion | Eff/Tar ratio | Target cells (% specific lysis) | | | | | | | |
|---|---|---|---|---|---|---|---|---|---|
| | | D122 | 77.8 | 19.2 | 85 | 95 | EL-4 | YAC | P815 |
| D122 | 100:1 | 0 | 0 | 0 | 0 | 0 | 0 | 0 | 0 |
| | 50:1 | 0 | 0 | 0 | 0 | 0 | 0 | 0 | |
| $K^b$77.8 | 100:1 | 9 | 26 | 5 | 12 | 13 | 0 | 0 | 0 |
| | 50:1 | 0 | 16 | 2 | 12 | 8 | 0 | 0 | |
| $K^d$19.2 | 100:1 | 2 | 26 | 36 | 41 | 45 | 0 | 0 | 0 |
| | 50:1 | 0 | 13 | 21 | 22 | 25 | 0 | 0 | |
| Kdb85 | 100:1 | 26 | 38 | 36 | 51 | 42 | 0 | 0 | |
| | 50:1 | 19 | 34 | 36 | 39 | 41 | 0 | 0 | |
| Kdb95 | 100:1 | 24 | 32 | 43 | 46 | 58 | 0 | 0 | 0 |
| | 50:1 | 14 | 26 | 24 | 37 | 30 | 0 | 0 | |

In vitro lytic activity of CTLs elicited by D122, Single transfectants ($K^b$ 77.8 and $K^d$ 19.2) and double transfectants (Kd,b 85 and Kd,b 95). CB6/F1 mice were immunized three times at 7-day intervals by i.p injection of $2 \times 10^6$ irradiated and mitomycin C treated cells. 10 days later spleen cells were restimulated in vitro with the tumor cells from the same source, irradiated and mitomycin C treated as before, for 5 days (see Example 5). Data show percent specific lysis obtained with effector-to-target ratios of 100:1 and 50:1. Target cells labeled with $^{35}S$ methionine were reacted in a 16 hr assay with effector cells. The cytolytic activity on EL-4, YAC and P-815 target cells was determined after 5 hrs. Error percentages were under 5% of the mean values of the triplicates.

TABLE 19

| Immuniztion | Eff/Tar ratio | Target cells (% specific lysis) | | | | | | | |
|---|---|---|---|---|---|---|---|---|---|
| | | D122 | 77.8 | 4.1 | K-2 | 72 | EL-4 | YAC | L-cells |
| D122 | 100:1 | 0 | 4 | 0 | 0 | 0 | 0 | 0 | 0 |
| | 50:1 | 0 | 2 | 0 | 0 | 0 | 0 | 0 | 0 |
| $K^b$77.8 | 100:1 | 6 | 33 | 14 | 45 | 21 | 0 | 0 | 0 |
| | 50:1 | 6 | 36 | 11 | 42 | 24 | 0 | 0 | 0 |
| $K^k$ 4.1 | 100:1 | 40 | 14 | 45 | 27 | 44 | 0 | 0 | 0 |
| | 50:1 | 28 | 5 | 42 | 24 | 40 | 0 | 0 | 0 |
| K-2 | 100:1 | 58 | 42 | 48 | 47 | 45 | 0 | 0 | 0 |
| | 50:1 | 40 | 29 | 44 | 34 | 32 | 0 | 0 | 0 |
| Kkb72 | 100:1 | 57 | 56 | 65 | 47 | 62 | 0 | 0 | 0 |
| | 50:1 | 55 | 55 | 58 | 47 | 51 | 0 | 0 | 0 |

In vitro lytic activity of CTLs elicited by D122, Single transfectants ($K^b$ 77.8 and $K^k$ 4.1) and double transfectants (K-2 and Kk,b 72). C3B6/F1 mice were immunized three times at 7-day intervals by i.p injection of $2 \times 10^6$ irradiated and mitomycin C treated cells. 10 days later spleen cells were restimulated in vitro with the tumor cells from the same source, irradiated and mitomycin C treated as before, for 5 days (see Example 5). Data show percent specific lysis obtained with effector to target ratios of 100:1 and 50:1. Target cells labeled with $^{35}S$ methionine were reacted in a 16 hr assay with effector cells. The cytolytic activity on EL-4, YAC and L-cells (target cells) was determined after 5 hrs. Error percentages were under 5% of the mean values of the triplicates.

TABLE 20

| Immuniztion | Eff/Tar ratio | Target cells (% specific lysis) | | | | | | |
|---|---|---|---|---|---|---|---|---|
| | | D122 | 77.8 | 25.1 | 4 | 68 | EL-4 | YAC |
| D122 | 100:1 | 0 | 0 | 0 | 0 | 0 | 0 | 0 |
| | 50:1 | 0 | 0 | 0 | 0 | 0 | 0 | 0 |
| $K^b$77.8 | 100:1 | 11 | 22 | 17 | 31 | 21 | 0 | 0 |
| | 50:1 | 10 | 7 | 13 | 28 | 9 | 0 | 0 |
| DKM25.1 | 100:1 | 16 | 19 | 19 | 31 | 16 | 0 | 0 |
| | 50:1 | 1 | 12 | 15 | 30 | 14 | 0 | 0 |
| Kbm1,b68 | 100:1 | 37 | 15 | 41 | 35 | 47 | 0 | 0 |
| | 50:1 | 24 | 13 | 20 | 27 | 32 | 0 | 0 |

In vitro lytic activity of CTLs elicited by D122, Single transfectants ($K^b$ 77.8 and DKM 25.1) and double transfectants (Kbm1,b4 and Kbm1,b 68). (BLXBM1)/F1 mice were immunized three times at 7-day intervals by i.p injection of $2 \times 10^6$ irradiated and mitomycin C treated cells. 10 days later spleen cells were restimulated in vitro with the tumor cells from the same source; irradiated and mitomycin C treated as before, for 5 days (see Example 5). Data show percent specific lysis obtained with effector-to-target ratios of 100:1 and 50:1. Target cells labeled with $^{35}S$ methionine were reacted in a 16 hr assay with effector cells. The cytolytic activity on EL-4 and YAC target cells was determined after 5 hrs. Error percentages were under 5% of the mean values of the triplicates.
$K^{bm1}$ 25.1 is also named DKM 25.1

TABLE 21

| First inoculation | No. of mice without tumor | Second inoculation | No. of mice without tumor |
|---|---|---|---|
| C57BL/6 mice | | | |
| Kd,b 24 | 4/8 | D122 | 4/4 |
| Kd,b 70 | 5/8 | D122 | 5/5 |
| Kd,b 75 | 4/8 | D122 | 4/4 |
| Kd,b 80 | 4/8 | D122 | 4/4 |
| Kd,b 85 | 8/8 | D122 | 8/8 |
| Kd,b 95 | 8/8 | D122 | 8/8 |
| Control | — | D122 | 0/8 |
| K-2 | 8/8 | D122 | 8/8 |
| Kk,b 72 | 8/8 | D122 | 8/8 |
| kk,b 74 | 8/8 | D122 | 8/8 |
| Kk,b 83 | 8/8 | D122 | 8/8 |
| Control | — | D122 | 0/8 |

TABLE 21-continued

| First inoculation | No. of mice without tumor | Second inoculation | No. of mice without tumor |
|---|---|---|---|
| CB6/F1 mice | | | |
| Kd,b 24 | 8/8 | D122 | 8/8 |
| Kd,b 70 | 3/8 | D122 | 3/8 |
| Kd,b 80 | 2/8 | D122 | 2/8 |
| Kd,b 75 | 8/8 | D122 | 8/8 |
| Kd,b 85 | 4/8 | D122 | 4/8 |
| Kd,b 95 | 5/8 | D122 | 5/8 |
| Control | — | D122 | 0/8 |
| C3B6/F1 mice | | | |
| K-2 | 8/8 | D122 | 8/8 |
| Kk,b 72 | 8/8 | D122 | 8/8 |
| Kk,b 83 | 8/8 | D122 | 8/8 |
| Control | — | D122 | 0/8 |

Growth of D122 cells in immunized mice. Mice that did not grow the primary tumor after 120–150 days were boosted by i.p. injection of $2 \times 10^6$ irradiated and mitomycin-C treated tumor cells as in the first inoculation. 10 days after the immunization, mice were challenged i.f.p. with D122 cells and growth of the parental D122 cells was measured.

We claim:

1. A cellular composition that provokes an immune response in a human patient when said cellular composition is used to treat a patient having a heterozygous haplotype, said cellular composition comprising:
   (a) tumor cells isolated from said patient to be treated into which at least two genes encoding MHC proteins of different haplotypes have been inserted, wherein said genes are expressed in said tumor cells and at least one of said MHC proteins has the same haplotype as a haplotype of the heterozygous patient to be treated; and
   (b) a pharmaceutically acceptable carrier.

2. The cellular composition according to claim 1 wherein said genes inserted into said tumor cells have been introduced on a single expression vector.

3. The cellular composition according to claim 2 wherein said expression vector is selected from the group consisting of a plasmid and a retroviral vector.

4. The cellular composition according to claim 1 wherein said genes inserted into said tumor cells have been introduced on different expression vectors.

5. The cellular composition of according to claim 4 wherein at least one of said expression vectors is selected from the group consisting of a plasmid and a retroviral vector.

6. The cellular composition according to claim 1, wherein said genes have been integrated into a chromosome of said tumor cell.

7. The cellular composition according to claim 1, wherein said genes are episomally retained in said tumor cell.

8. The cellular composition according to claim 1, wherein the tumor cells have been inactivated and thereby rendered nonreplicating by a treatment, said treatment comprising at least one treatment selected from the group consisting of irradiation inactivation and mitomycin C inactivation.

9. The cellular composition according to claim 1, wherein said genes have been inserted into said tumor cells by transfection.

10. The cellular composition of claim 1 wherein said composition comprises $1 \times 10^6$ to $1 \times 10^9$ tumor cells.

11. The cellular composition of claim 10 wherein said composition comprises $1 \times 10^7$ tumor cells.

12. The cellular composition of claim 1 wherein said composition is formulated as an injectable solution.

13. The cellular composition of claim 1 wherein said MHC proteins are selected from the group of class I MHC molecules HLA-A, HLA-B, and HLA-C.

14. A method of treating a patient suffering from a tumorous disease comprising administering the cellular composition according to claim 1 to said patient.

* * * * *